(12) United States Patent
Tsampazis et al.

(10) Patent No.: US 9,409,017 B2
(45) Date of Patent: Aug. 9, 2016

(54) DIAGNOSTIC TESTING AND ADAPTION

(71) Applicants: Kostas Tsampazis, North Ryde (AU); Adrian Robert Cryer, Pymble (AU)

(72) Inventors: Kostas Tsampazis, North Ryde (AU); Adrian Robert Cryer, Pymble (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 14/303,810

(22) Filed: Jun. 13, 2014

(65) Prior Publication Data

US 2015/0360028 A1 Dec. 17, 2015

(51) Int. Cl.
| | |
|---|---|
| *A61N 1/36* | (2006.01) |
| *A61N 1/05* | (2006.01) |
| *A61N 1/37* | (2006.01) |
| *A61N 1/08* | (2006.01) |
| *G01R 31/02* | (2006.01) |

(52) U.S. Cl.
CPC .......... *A61N 1/36032* (2013.01); *G01R 31/025* (2013.01); *A61B 2560/0276* (2013.01); *H04R 2225/67* (2013.01); *H04R 2460/00* (2013.01)

(58) Field of Classification Search
CPC ......... A61N 1/0541; A61N 1/08; A61N 1/36; A61N 1/36032; A61N 1/3605; A61N 1/36125; A61N 1/375; A61N 1/3752; A61N 1/3754
USPC ....................... 607/56, 57, 115, 116, 136, 137
See application file for complete search history.

(56) References Cited

U.S. PATENT DOCUMENTS

| | | | |
|---|---|---|---|
| 5,713,935 A | 2/1998 | Prutchi et al. | |
| 5,755,742 A | 5/1998 | Schuelke et al. | |
| 5,814,095 A * | 9/1998 | Muller | A61N 1/36032 607/56 |
| 5,897,577 A | 4/1999 | Cinbis et al. | |
| 6,978,171 B2 | 12/2005 | Goetz et al. | |
| 7,047,083 B2 | 5/2006 | Gunderson et al. | |
| 7,454,249 B1 | 11/2008 | Bornzin et al. | |
| 8,588,911 B2 | 11/2013 | Nygard et al. | |
| 8,768,479 B1 * | 7/2014 | Hood et al. | 607/57 |
| 2004/0176702 A1 * | 9/2004 | Stirnemann | 600/559 |
| 2006/0161227 A1 * | 7/2006 | Walsh et al. | 607/88 |
| 2006/0281435 A1 * | 12/2006 | Shearer et al. | 455/343.1 |
| 2007/0100407 A1 | 5/2007 | Armstrong | |
| 2008/0002841 A1 * | 1/2008 | Baker et al. | 381/113 |
| 2008/0024140 A1 * | 1/2008 | Henson et al. | 324/536 |
| 2008/0045804 A1 * | 2/2008 | Williams | 600/300 |
| 2008/0091308 A1 * | 4/2008 | Henson et al. | 700/293 |
| 2008/0194953 A1 * | 8/2008 | Kerber | 600/437 |
| 2009/0102296 A1 * | 4/2009 | Greene et al. | 307/149 |
| 2009/0326600 A1 * | 12/2009 | Kracker | A61N 1/3706 607/27 |
| 2010/0152623 A1 * | 6/2010 | Williams | 600/595 |
| 2011/0043217 A1 | 2/2011 | Tsampazis et al. | |
| 2011/0077698 A1 | 3/2011 | Tsampazis et al. | |
| 2011/0087085 A1 * | 4/2011 | Tsampazis et al. | 600/379 |
| 2011/0098785 A1 * | 4/2011 | Mishra | A61N 1/36032 607/57 |
| 2011/0112443 A1 * | 5/2011 | Williams | 600/595 |
| 2011/0160799 A1 * | 6/2011 | Mishra et al. | 607/57 |
| 2011/0224976 A1 * | 9/2011 | Taal et al. | 704/205 |
| 2011/0262740 A1 * | 10/2011 | Martin et al. | 428/332 |
| 2011/0264010 A1 * | 10/2011 | Williams | 600/595 |

(Continued)

*Primary Examiner* — Christopher A Flory
(74) *Attorney, Agent, or Firm* — Edell, Shapiro & Finnan, LLC

(57) ABSTRACT

Presented herein is diagnostic and adaptive circuitry for use in an implantable medical system (prosthesis) having at least two physically separate implantable modules (packages) that are electrically connected by a lead assembly (cable). The diagnostic and adaptive circuitry is configured to execute testing and adaptive (corrective) functions.

23 Claims, 22 Drawing Sheets

(56) References Cited

U.S. PATENT DOCUMENTS

| | | | |
|---|---|---|---|
| 2012/0029593 A1* | 2/2012 | Calle et al. | 607/57 |
| 2012/0029594 A1* | 2/2012 | Chapa et al. | 607/57 |
| 2012/0029595 A1* | 2/2012 | Kruger et al. | 607/57 |
| 2012/0029930 A1* | 2/2012 | Calle et al. | 705/2 |
| 2012/0053656 A1* | 3/2012 | Chapa et al. | 607/57 |
| 2012/0143284 A1* | 6/2012 | Capcelea et al. | 607/57 |
| 2012/0300953 A1 | 11/2012 | Mauch et al. | |
| 2012/0303096 A1* | 11/2012 | Kulkarni et al. | 607/57 |
| 2012/0316454 A1* | 12/2012 | Carter | 600/547 |
| 2013/0066392 A1* | 3/2013 | Simon | A61N 1/40 307/45 |
| 2013/0073002 A1* | 3/2013 | Nygard et al. | 607/57 |
| 2013/0204174 A1* | 8/2013 | Olde | A61M 1/3653 604/6.11 |
| 2013/0204326 A1* | 8/2013 | Vanpoucke | 607/57 |
| 2013/0226254 A1 | 8/2013 | Walling et al. | |
| 2013/0304157 A1* | 11/2013 | Smith et al. | 607/57 |
| 2014/0200630 A1* | 7/2014 | Mishra | A61N 1/36032 607/57 |
| 2015/0224312 A1* | 8/2015 | Platz | A61N 1/36032 607/57 |
| 2015/0290458 A1* | 10/2015 | Hartley | A61N 1/37217 607/57 |

\* cited by examiner

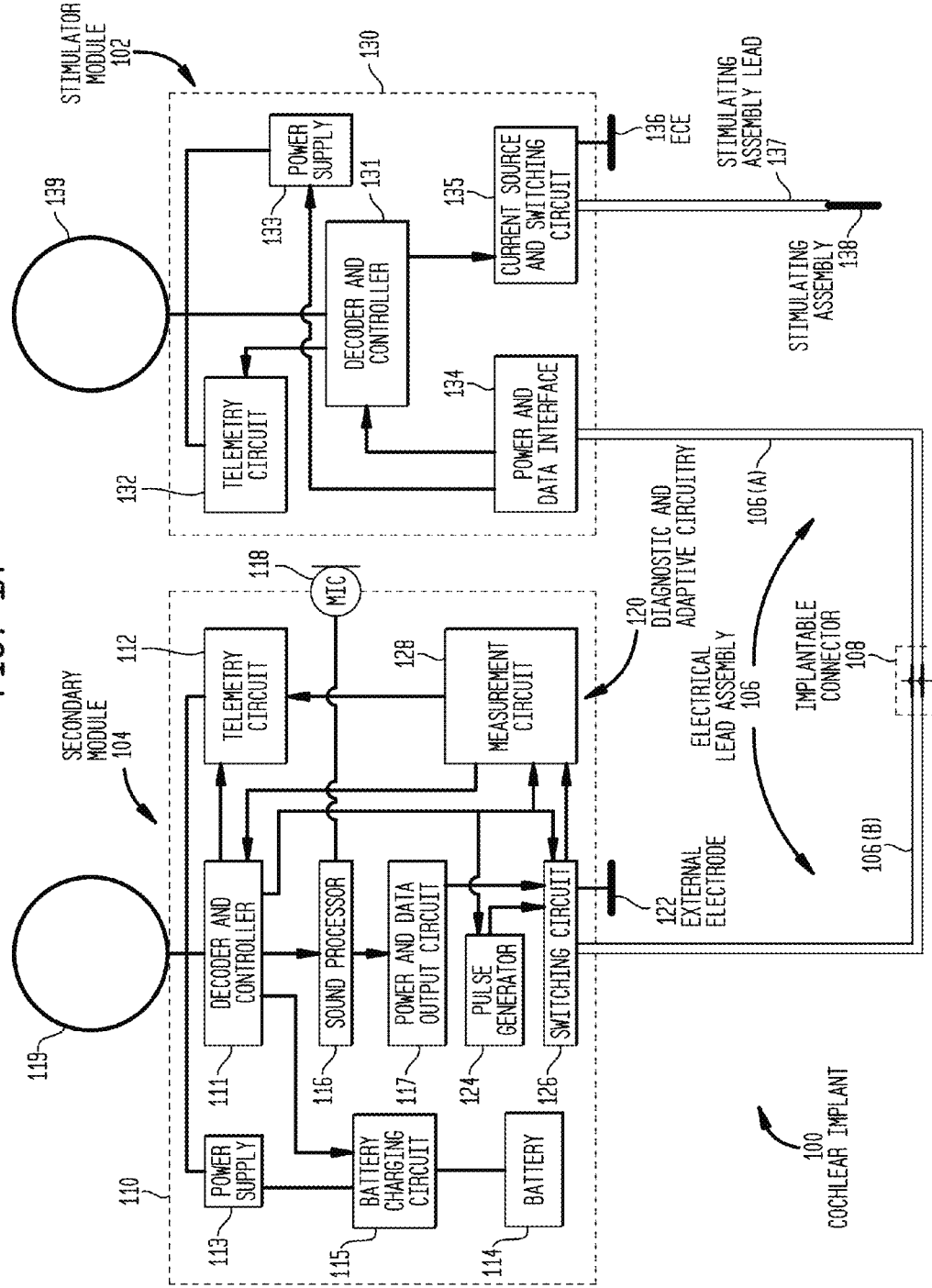

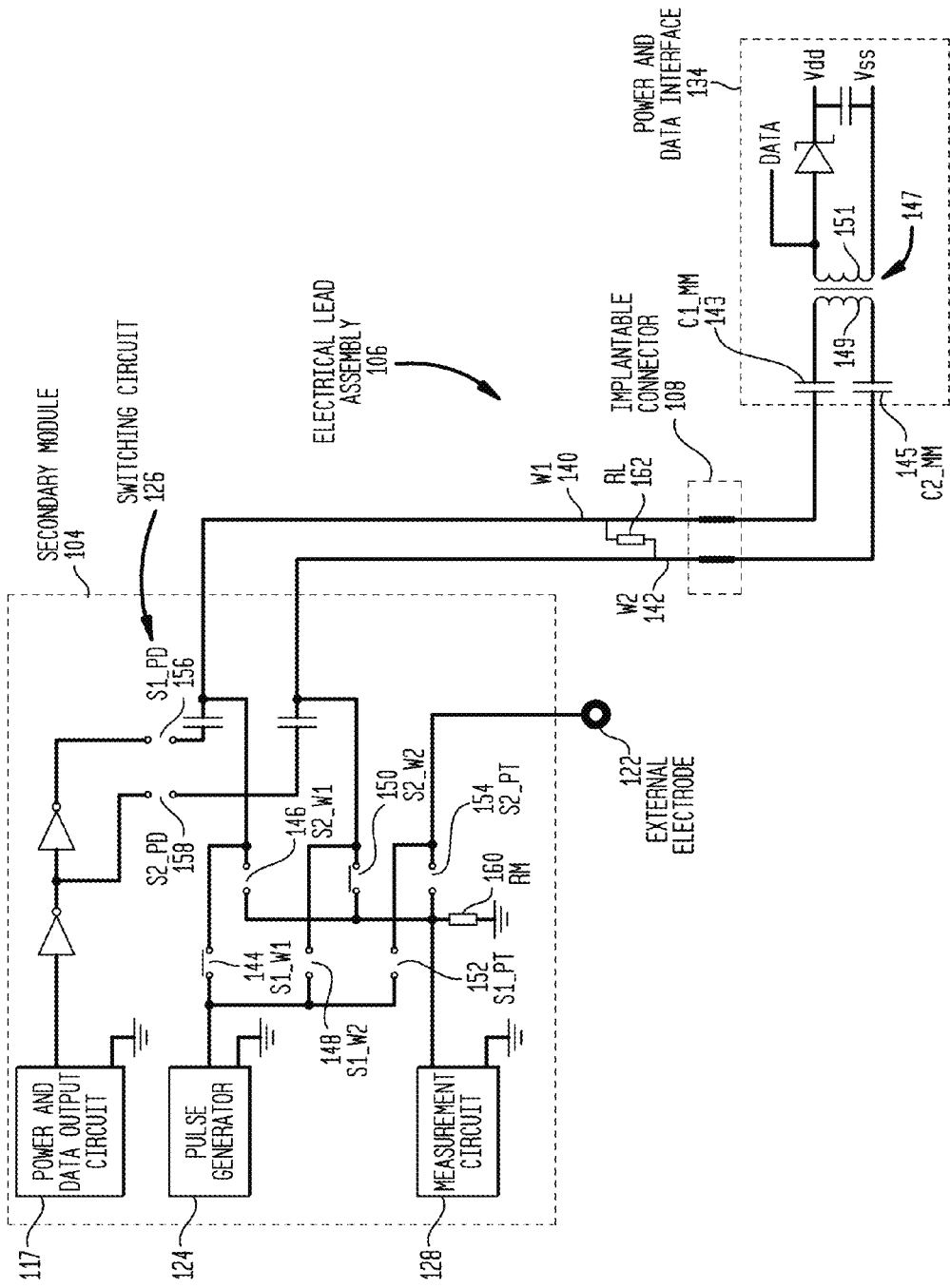

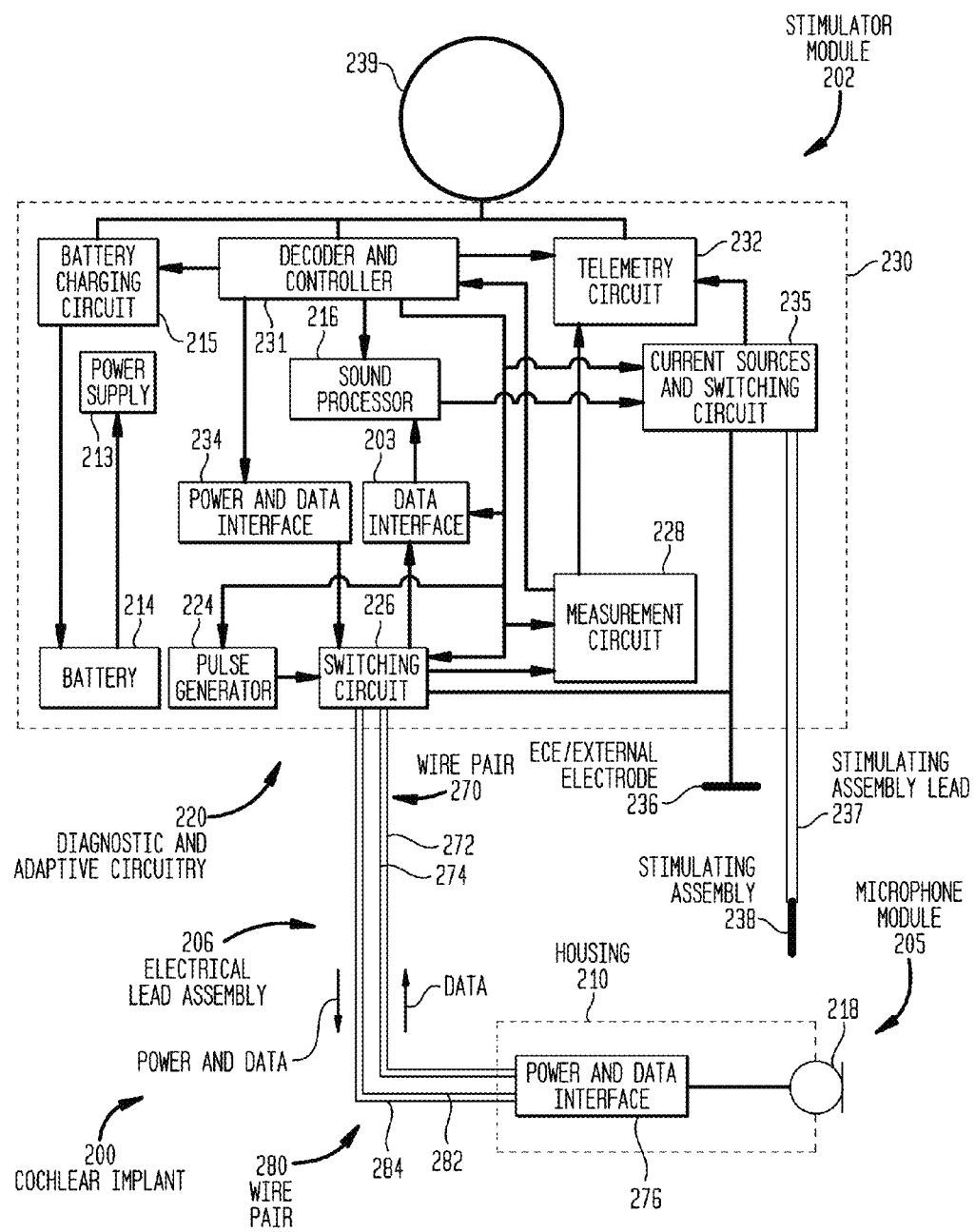

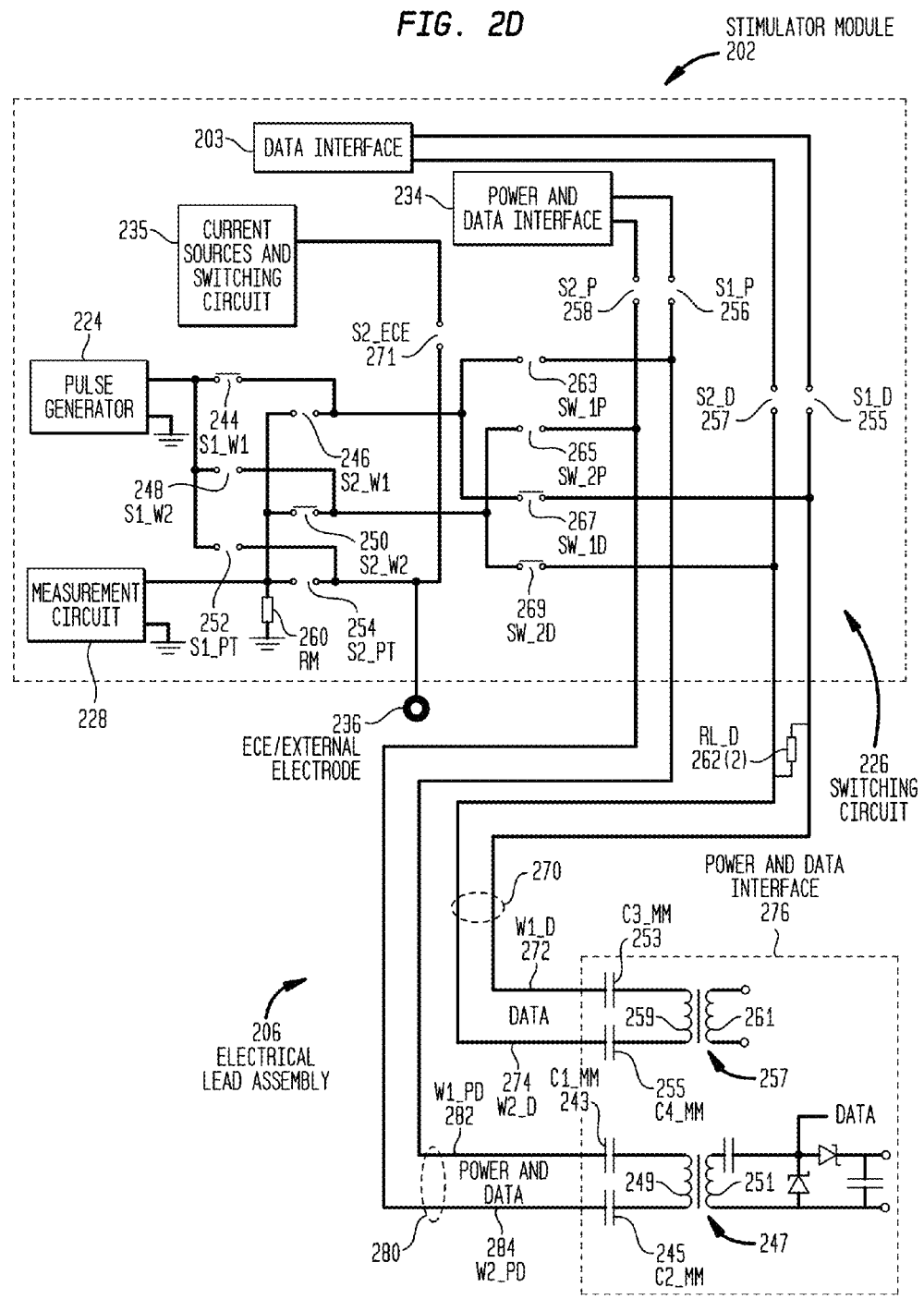

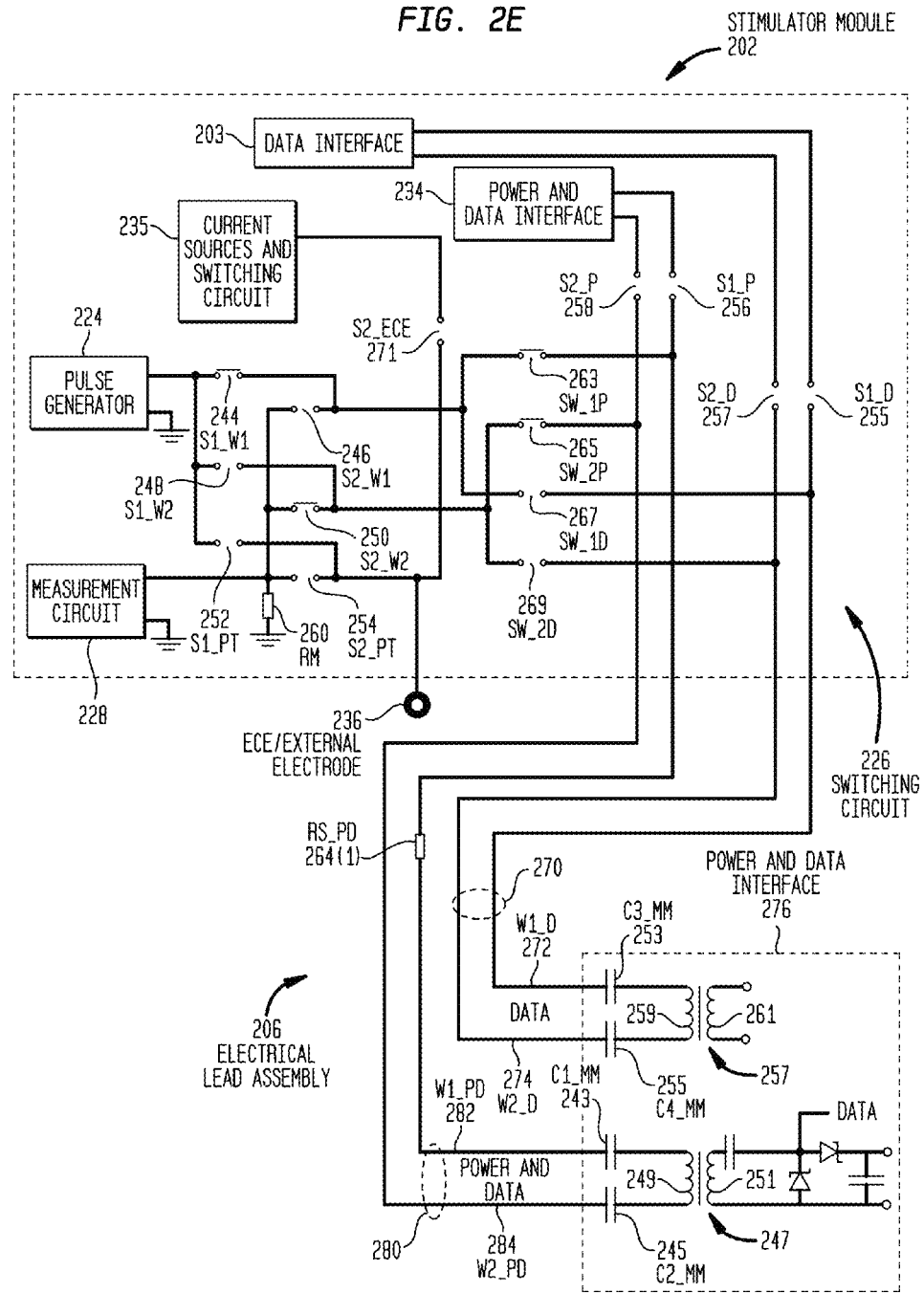

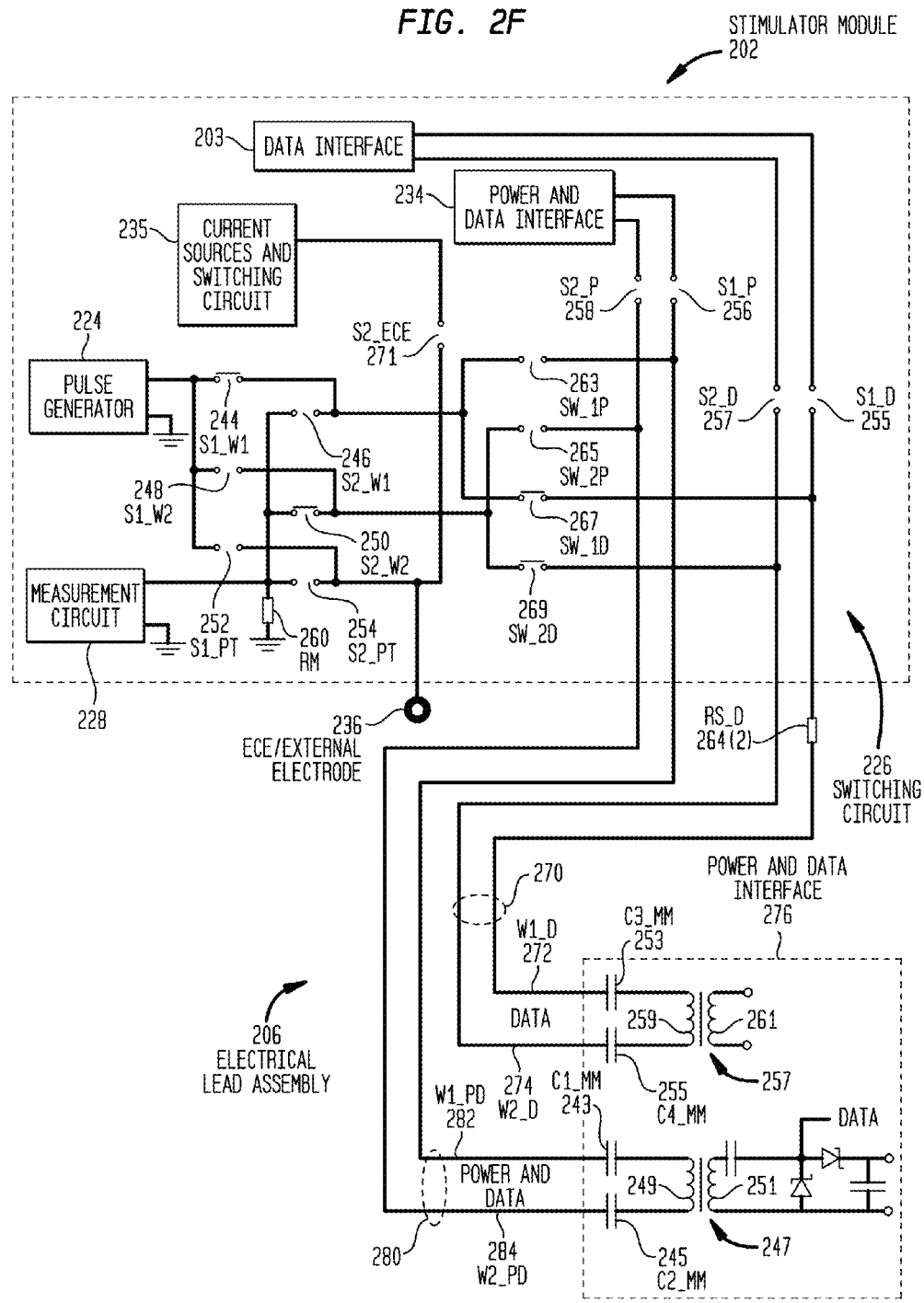

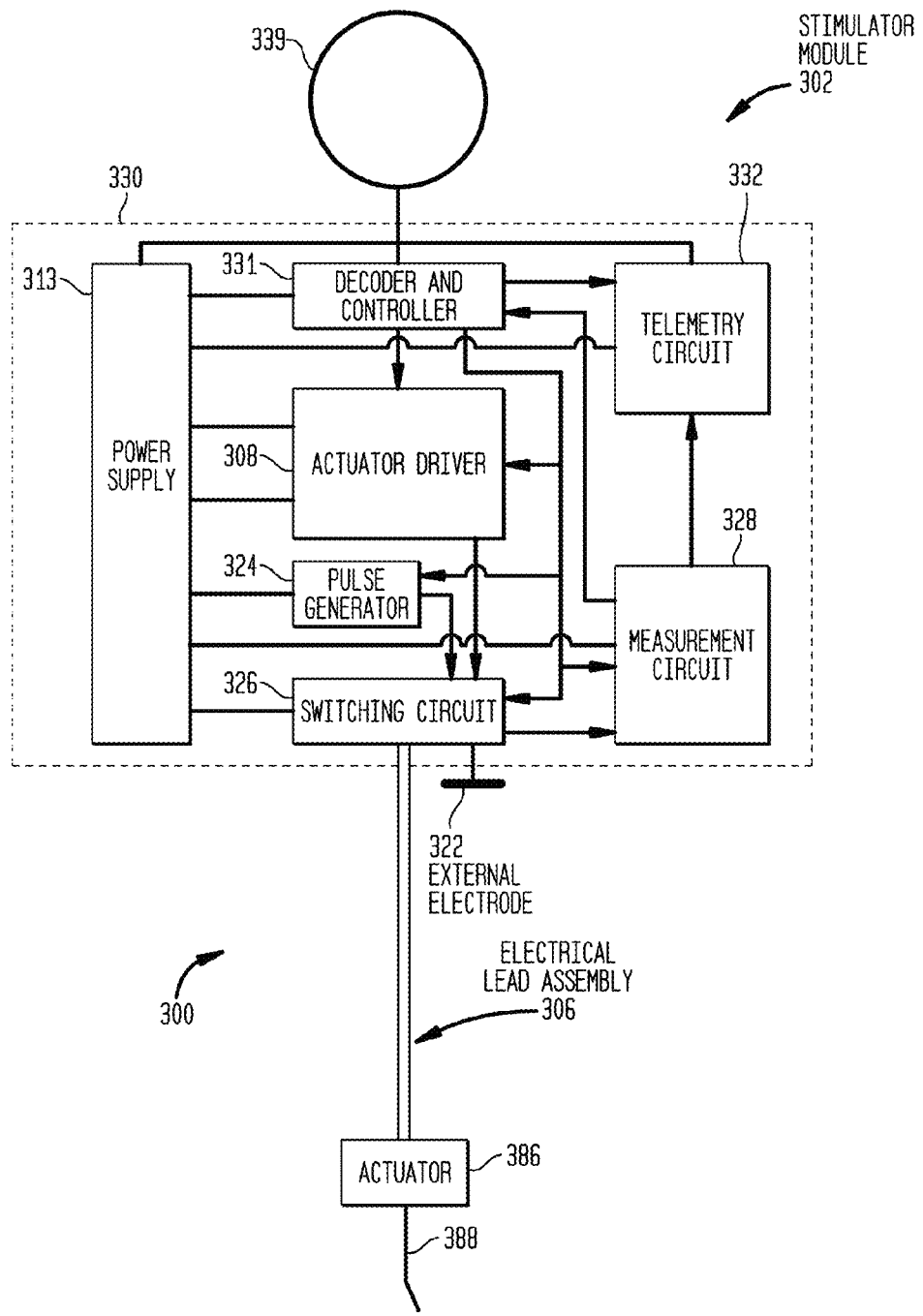

DIAGNOSTIC TESTING AND ADAPTION

BACKGROUND

1. Field of the Invention

The present invention relates generally to implantable medical devices.

2. Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

SUMMARY

In one aspect an implantable hearing prosthesis is provided. The implantable hearing prosthesis comprises a first implantable component, a second implantable component electrically connected to the first implantable component, and diagnostic and adaptive circuitry configured to perform diagnostic tests on the electrical connection between the first and second implantable components and to perform adaptive functions based on the results of the diagnostic tests.

In another aspect a method performed in an implantable hearing prosthesis comprising first and second physically separate implantable components connected by a lead assembly is provided. The method comprises performing one or more diagnostic tests to evaluate an electrical connection between first and second implantable components provided by the lead assembly, and based on the results of the one or more diagnostic tests, performing one or more adaptive functions to adjust the electrical connection between the first and second implantable components.

In a further aspect an implantable hearing prosthesis is provided. The implantable hearing prosthesis comprises first and second physically separate implantable components, a cable electrically connecting the first and second implantable components, and a circuit in the first implantable component configured to evaluate electrical attributes of the cable and to adapt current flow through the cable based on the evaluation of the electrical attributes.

BRIEF DESCRIPTION OF THE DRAWINGS

Embodiments of the present invention are described herein in conjunction with the accompanying drawings, in which:

FIG. 1A is a block diagram of a cochlear implant configured to perform testing and adaptive functions in accordance with embodiments presented herein;

FIG. 1D is a schematic circuit diagram illustrating a configuration for diagnostic and adaptive circuitry in accordance with embodiments presented herein;

FIG. 1G is a schematic circuit diagram illustrating a configuration for diagnostic and adaptive circuitry in accordance with embodiments presented herein;

FIG. 2A is a block diagram of another cochlear implant configured to perform testing and adaptive functions in accordance with embodiments presented herein;

FIG. 2D is a schematic circuit diagram illustrating a configuration for diagnostic and adaptive circuitry in accordance with embodiments presented herein;

FIG. 2E is a schematic circuit diagram illustrating a configuration for diagnostic and adaptive circuitry in accordance with embodiments presented herein;

FIG. 2F is a schematic circuit diagram illustrating a configuration for diagnostic and adaptive circuitry in accordance with embodiments presented herein;

FIG. 3A is a block diagram of a direct acoustic cochlear stimulator configured to perform testing and adaptive functions in accordance with embodiments presented herein;

DETAILED DESCRIPTION

Figure 1B:
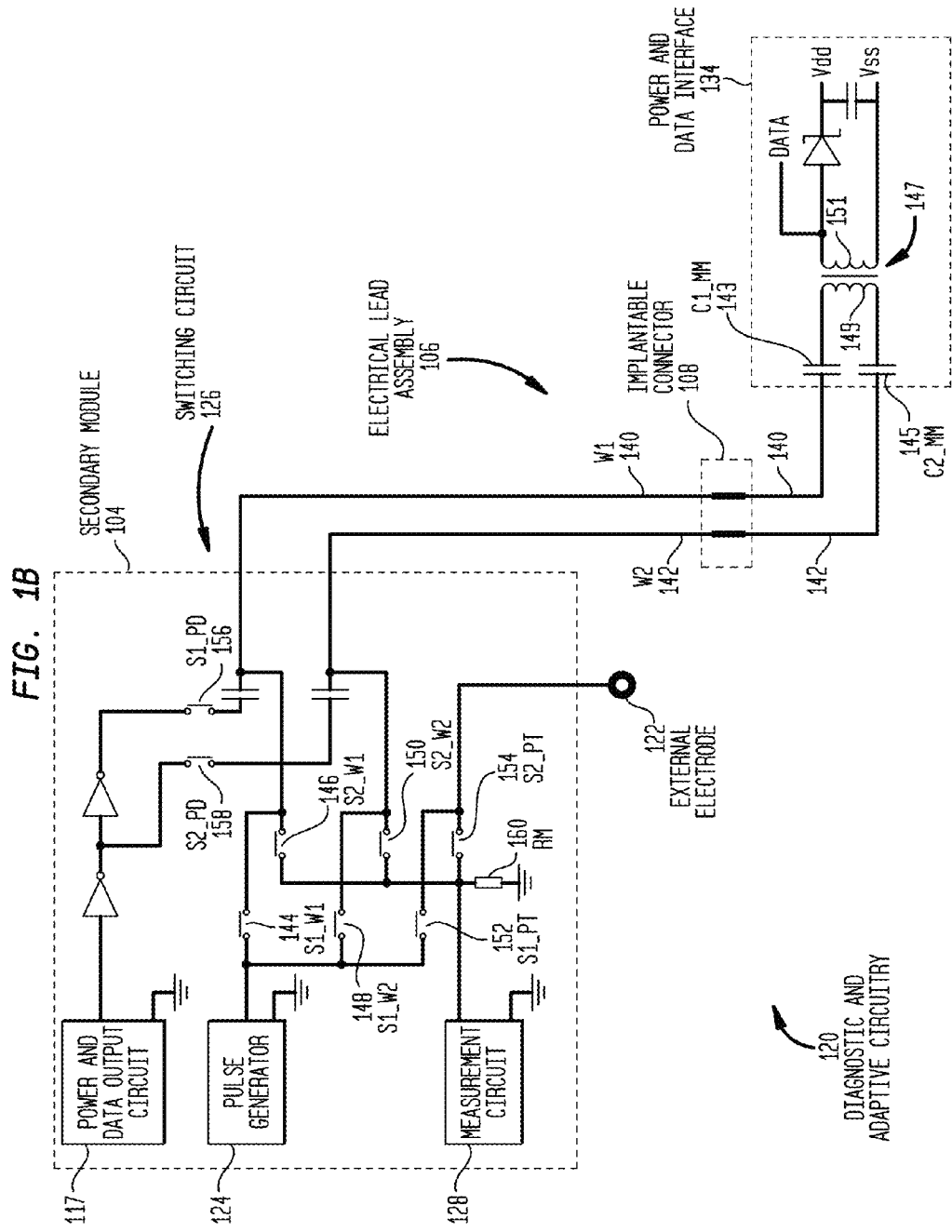
FIG. 1B is a schematic circuit diagram illustrating further details of an electrical lead assembly, stimulator module, and diagnostic and adaptive circuitry in accordance with embodiments presented herein.

Presented herein is diagnostic and adaptive circuitry for use in an implantable medical system (prosthesis) having at least two physically separate implantable modules (packages) that are electrically connected by a lead assembly (cable). The diagnostic and adaptive circuitry is configured to execute testing and adaptive (corrective) functions. The testing functions can include, for example, (1) detecting electrical leakage between two insulated wires (leads/conductors) of the lead assembly, (2) confirming electrical continuity through the insulated wires of the lead assembly, and/or (3) detecting electrical leakage between an insulated wire and a reference point outside of the lead assembly (e.g., leakage between a wire and the recipient's tissue/body fluid). The adaptive functions can include, for example, the automatic reduction and/or termination of current flow in the respective tested circuit, an increase in current flow, etc.

The diagnostic and adaptive circuitry may provide one or more benefits when used in an implantable hearing prosthesis. For example, if the insulation of the cable connection is inadequate, then stray currents can be detected by the microphone which in turn can interfere with the audio signal which drives the stimulator unit, and can present a hazardous risk to the recipient. The diagnostic and adaptive circuitry may be used to detect such stray currents and take corrective action. Additionally, a short circuit between two wires within a lead assembly can cause the release of a significant amount of heat into the recipient's tissue. Again, the diagnostic and adaptive circuitry may be used to detect such short circuits and take action to terminate current flow before the short circuit causes damage to the recipient's tissue.

As described below, the diagnostic and adaptive circuitry may be used in any implantable hearing prosthesis that has two or more physically separate implantable components connected by an electrical connection (e.g., lead assembly, cable, connector, etc.) comprising one or more wire pairs (e.g., any a two-wire link, four-wire link, etc.). However, merely for ease of description, the diagnostic and adaptive circuitry in accordance with embodiments of the present invention will be described with reference to three illustrative implantable hearing prosthesis, namely two different cochlear implants and one direct acoustic cochlear stimulator.

FIG. 1A is a block diagram of an implantable hearing prosthesis in the form of a cochlear implant 100 that includes diagnostic and adaptive circuitry in accordance with embodiments presented herein. In the example of FIG. 1A, the cochlear implant 100 includes a stimulator module (main module) 102 and a physically separate secondary module (upgrade module) 104. The stimulator module 102 and secondary module 104 are each hermetically sealed packages that are electrically connected by an electrical lead assembly (cable) 106. The lead assembly 106 includes a first segment 106(A) extending from the stimulator module 102 and a second segment 106(B) extending from the secondary module 104. The first segment 106(A) and the second segment 106(B) are electrically connected by an implantable connector 108. The implantable connector 108 is a hermetically sealed multi-connection electrical interface between the first segment 106(A) and the second segment 106(B). The implantable connector 108 is a releasable connector that enables the secondary module 104 to be completely electrically and physically separated from the stimulator unit 102. As such, the secondary module 104 may be repositioned and/or explanted without disturbing the implanted location of the stimulator module 102.

The secondary module 104 includes a hermetically sealed housing 110. Disposed in the housing 110 is a decoder and controller 111 (referred to herein simply as a controller 111), a telemetry circuit 112, a power supply 113, a battery 114, a battery charging circuit 115, a sound processor 116, and a power and data output circuit 117. A microphone 118 may be partially disposed in the housing 110 or may be positioned external to the housing 110 and connected to components within the housing via a feedthrough. An implantable coil (antenna) 119 is also connected to one or more components within the housing 110 via a feedthrough. For ease of illustration, the feedthroughs in secondary module 104 and stimulator module 102 have been omitted from the drawings.

The secondary module 104 also includes an external electrode 122, a pulse generator 124, a switching circuit 126, and a measurement circuit 128. The pulse generator 124, the switching circuit 126, and the measurement circuit 128 are disposed within the housing 110. The external electrode 122 is connected to the switching circuit 126 via a feedthrough (not shown in FIG. 1A). The external electrode 122, switching circuit 126, pulse generator 124, measurement circuit 128, telemetry circuit 112, and controller 111 collectively form diagnostic and adaptive circuitry 120. As described further below, the switching circuit 126 is configured to switch/select between a stimulation operational mode (i.e., a mode during which data and/or power is supplied to the stimulator module 102) and a diagnostic operational mode (i.e., a mode during which testing and adaptive operations are performed). The pulse generator 124 is configured to source/generate test pulses during the diagnostic operational mode, while the measurement circuit 128 is configured to measure the voltage response of the electrical lead assembly 106 to test pulses. The telemetry circuit 112 is configured to supply test results and/or indications of corrective actions performed to an external device (not shown) that is part of, or operates in conjunction with, the cochlear implant 100. The controller 111 is configured to control/drive the other components of the diagnostic and adaptive circuitry 120.

The stimulator module 102 includes a hermetically sealed housing 130. Disposed in the housing 130 is a decoder and controller 131 (referred to herein as controller 131), a telemetry circuit 132, a power supply 133, a power and data interface 134, and a current source and switching circuit 135 (referred to herein as stimulator 135). An extra-cochlear electrode (ECE) 136, stimulating assembly lead 137, and an implantable coil (antenna) 139 are each connected to one or more components within the housing 130 via respective feedthroughs (not shown). The stimulating assembly lead 137 is connected to a stimulating assembly 138 that is configured to be implanted within a recipient's cochlea.

It is be appreciated that in certain embodiments there may be two extra-cochlear electrodes. For simplicity, only one extra-cochlear electrode is shown. In one specific example, in addition to ECE 136, the housing 130 may be a titanium member that operates as a second extra-cochlear electrode.

In operation, the implantable coil 119 is configured to receive power and/or data from the external device (not shown) that is part of, or operates in conjunction with, the cochlear implant 100. The received power may be used to recharge battery 114, while the received data may be processed by the sound processor 116. That is, the sound processor 116 is configured to convert the received data, which represents received sound, into coded signals. These coded signals are then sent to stimulator module 102 for use in outputting a series of stimulation signals (electrical stimulation pulses) that, when delivered to the recipient via the stimulating assembly 138, evoke perception of the received sound. In this way, cochlear implant 100 stimulates the recipient's auditory nerve cells, bypassing absent or defective hair cells that normally transduce acoustic vibrations into neural activity.

The implantable coil 139 attached to stimulator module 102 operates as an optional power and data coil. That is, implantable coil 139 may be selectively used to receive power and data from the external device (e.g., sound processor). The stimulator module 102 can work independently from the secondary module 104 (when the secondary module 104 is switched off or not in use) by receiving power and data from the external device.

As noted, the stimulator module 102 is connected to the secondary module 104 via the electrical lead assembly 106. More specifically, the electrical lead assembly segment 106(B) is connected to the switching circuit 126 in secondary module 104 (via a feedthrough), while the electrical lead assembly segment 106(A) is connected to the power and data interface 134 within stimulator module 102 (again via a feedthrough). The electrical lead assembly 106 is a two-wire power/data link (i.e., one pair of wires) that is selectively used to carry the coded signals and power to the stimulator module 102.

The diagnostic and adaptive circuitry 120 is configured to execute testing and adaptive (corrective) functions to test the integrity of the electrical lead assembly 106, including the connector 108, and to automatically adjust the parameters and/or conditions of the power/data transmission in order to, for example, prevent high (short circuit) currents or to compensate for a loss of power due to increased (high) impedance of the two-wire link. The diagnostic and adaptive functions can be run automatically every time when the cochlear implant 100 is turned on, at periodic intervals during operation, in response to a received command, etc.

FIG. 1B is a schematic diagram illustrating further details of the electrical lead assembly 106 and part of the diagnostic and adaptive circuitry 120. For ease of illustration, only the power and data interface 134 of stimulator module 102 is shown in FIG. 1B. Similarly, only a portion of secondary module 104 is shown in FIG. 1B.

As shown in FIG. 1B, the electrical lead assembly 106 includes a first wire (W1) 140 and a second wire (W2) 142. As noted above, the electrical lead assembly 106 includes two segments 106(A) and 106(B) connected by an implantable connector 108. As such, the wires 140 and 142 also each include two discrete segments 140(A)/140(B) and 142(A)/142(B) in the segments 106(A) and 106(B), respectively. For ease of description and unless specified otherwise, reference to "wire 140" or "wire 142" refers to the portions of the wires in both of segments 106(A) and 106(B).

In the example of FIG. 1B, power and data interface 134 of stimulator module 102 is a transformer coupled interface 134. More specifically, wire 140 terminates at capacitor 143 (C1_MM), while wire 142 terminates at capacitor 145 (C2_MM). Capacitors 143 and 145 are coupled to a primary coil 149 of the transformer 147. Transformer 147 also comprises a secondary coil 151.

Figure 1C:
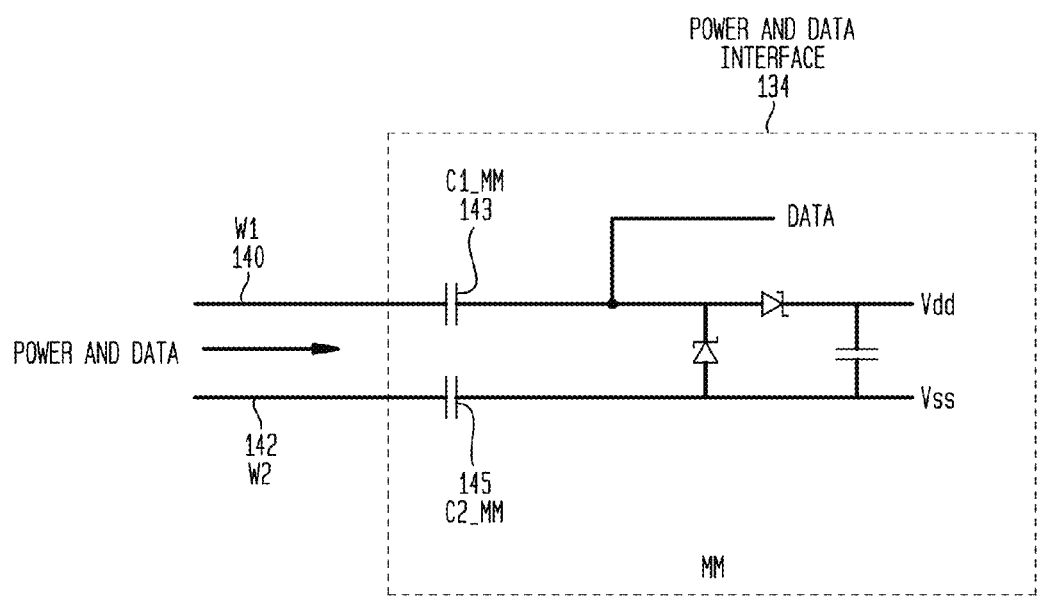
FIG. 1C is a schematic circuit diagram illustrating a power and data interface of a stimulator module in accordance with embodiments presented herein.

It is to be appreciated that the transformer coupled arrangement for power and data interface 134 shown in FIG. 1B is merely illustrative and that other arrangements are possible. For example, FIG. 1C illustrates an alternative arrangement where the power and data interface 134 of stimulator module 102 is a capacitor coupled interface. The capacitor coupled interface of FIG. 1C may be used in place of the transformer coupled interface without loss of functionality. Merely for ease of illustration, embodiments are generally illustrated herein in use with a transformer coupled interface 134.

Returning to the example of FIG. 1B, the switching circuit 126 includes a number of switches that can be selectively activated (closed) to enable the diagnostic and/or adaptive functions of the diagnostic and adaptive circuitry 120. First, the switching circuit 126 includes a switch 144 (S1_W1) and a switch 146 (S2_W1) that are associated with wire 140 (W1). Additionally, the switching circuit 126 includes a switch 148 (S1_W2) and a switch 150 (S2_W2) that are associated with wire 142 (W2). Furthermore the switching circuit 126 includes switch 152 (S1_PT) and switch 154 (S2_PT) that are associated with the external electrode 122. As described further below, the external electrode 122 is in contact with the recipient's tissue and/or body fluid and is used to detect/measure leakage current from W1 or W2 to the body.

The switching circuit 126 also includes switch 156 (S1_PD) and switch 158 (S2_PD) that are associated with the power and data output circuit 117. Switch S1_PD is configured to connect wire 142 to the power and data output circuit 117, while the switch S2_PD is configured to connect the wire 142 to the power and data output circuit 117.

During the stimulation operational mode, the switching circuit 126 is configured such that power/data signals are applied to the two-wire link (wires W1, W2) through switches 156 and 158. That is, switches 156 and 158 are closed while the other switches are open so as to disconnect pulse generator 124 and measurement circuit 128 from the two-wire link. During the diagnostic operational mode, the switching circuit 126 may have a number of different configurations/arrangements depending on the diagnostic test that is performed. FIGS. 1D-1G illustrate the configurations of switching circuit 126 during different diagnostic tests.

A first type of diagnostic test may be performed to detect low impedance (indicating a short circuit) between the wires 140 and 142 inside of the electrical lead assembly 106. This type of test, sometimes referred to herein as an "internal leakage current test," evaluates the electrical insulation of the wires 140 and 142 to determine if a short circuit is present between the wires. The configuration of switching circuit 126 to perform the internal leakage current test is shown in FIG. 1D.

FIG. 1D illustrates a resistor 162 (RL) within electrical lead assembly 106. The resistor 162 shown in FIG. 1D is not an actual resistor, but instead it represents the impedance (resistance) between the two wires 140 and 142. To perform the internal leakage current test (i.e., measure the leakage current between the wires 140 and 142), a long duration voltage pulse is applied to the wires 140 and 142 of the implantable connector through a measurement resistor 160 (RM). Initially, current flows from the pulse generator 124 through switch 144 along wire 140 through capacitor 143, to the primary coil 149 of the transformer 147. The current returns from the primary coil 149 through capacitor 145, along wire 142, through switch 150, and finally through the resistor 160 to a grounding element (ground).

The current through capacitors 143 and 145 and primary coil 149 exponentially decreases as the capacitors 143 and 145 are charging. When the capacitors 143 and 145 are completely charged, then the current flow through the capacitors and the primary coil 149 of the transformer 147 will cease. If there is no leakage current path between the wires 140 and 142 (i.e., RL=∞), then there will be no current flow after the capacitors 143 and 145 are been charged. As such, the voltage over the resistor 160, which is measured by the measurement circuit 128 after the capacitors 143 and 145 have charged, will be zero. If there is a leakage current path between the wires 140 and 142, then there will be a leakage current flow resulting in a voltage drop over the resistor 160.

The voltage across the resistor 160 is measured by the measurement circuit 128 at the end of the voltage pulse initiated by pulse generator 124. The voltage across the resistor 160 is also proportional to the amplitude of the leakage current between the wires 140 and 142. Therefore, the measurement circuit 128 can use the voltage level measured at the end of the pulse to quantify the leakage current between the wires 140 and 142. That is, the measurement circuit 128 is not only configured to detect the presence of current leakage between the wires 140 and 142, but rather may also be configured to determine a magnitude of the current leakage.

As noted above, the diagnostic and adaptive circuitry 120 is configured to perform adaptive functions based on the results of a diagnostic test. In the example of FIG. 1D, the detection of low impedance between the wires 140 and 142 indicates that there is a deterioration of the electrical insulation between the wires. As a result, the diagnostic and adaptive circuitry 120 can be configured to automatically limit or terminate the current flow through the electrical lead assembly 106 to prevent tissue damage resulting from heat released by the lead assembly 106 (i.e., resulting from a temperature rise due to short between the wires). That is, the excessive current consumption (due to the low impedance/short between the wires) can cause overheating of the electronic components (increase of the power dissipation) in module 104, resulting in temperature rise of the module 104. As such, the diagnostic and adaptive circuitry 120 provides high current protection for module 104 and the electrical lead assembly 106. The diagnostic and adaptive circuitry 120 may also be configured to transmit the results of the leakage current test to the external device (e.g., external processor, remote control, clinician equipment, etc.) via the telemetry circuit 112 and the implantable coil 119. The telemetry circuit 112 may be configured to transmit, for example, an indication that a current leakage has been detected, an indication of the magnitude of the current leakage, and/or an indication of the corrective action taken by the diagnostic and adaptive circuitry 120. The transmission by the telemetry circuit 112 may occur in real-time (i.e., if an external device is present) or the transition may occur at a later time. As such, the diagnostic and adaptive circuitry 120 may have the ability to temporarily store testing results for subsequent transmission/upload to an external device.

A second type of diagnostic test may be performed by the diagnostic adaptive circuitry 120 to detect low (normal) impedance, high impedance (faulty condition), or open circuit (faulty condition) at each of the wires 140 or 142. This test is sometimes referred to herein as a "continuity test" and tests the electrical continuity of the wires 140 and 142 and the implantable connector 108. The configuration to perform the continuity test is shown in FIG. 1E.

Figure 1E:
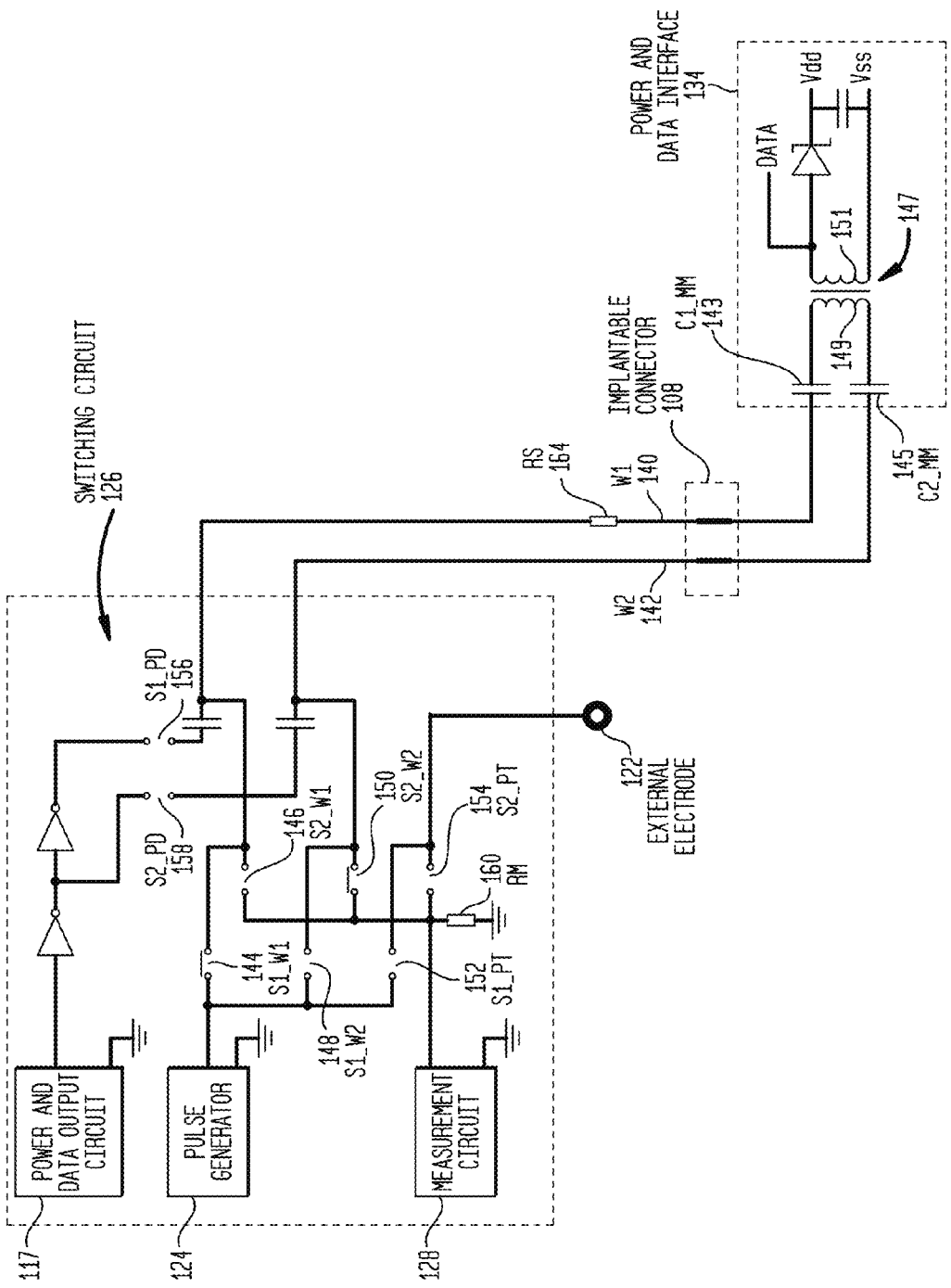
FIG. 1E is a schematic circuit diagram illustrating a configuration for diagnostic and adaptive circuitry in accordance with embodiments presented herein.

FIG. 1E illustrates a resistor 164 (RS) within electrical lead assembly 106. The resistor 164 shown in FIG. 1E is not an actual resistor, but instead represents the impedance (resistance) along the electrical path defined by the wires 140 and 142. To perform the continuity test, a voltage pulse is applied to the wires 140 and 142 of the implantable lead assembly through the measurement resistor 160. Initially, current flows from the pulse generator 124 through switch 144, along wire 140, through capacitor 143 to the primary coil 149 of the transformer 147. The current returns from the primary coil 149 through capacitor 145, along wire 142, through switch 150, through the resistor 160 to ground.

The initial amplitude of the current (i.e., the initial current peak), measured at resistor 160 by measurement circuit 128, is proportional to the impedance of the current path (i.e., the path defined by switch 144, wire 140, capacitor 143, primary coil 149, capacitor 145, wire 142, switch 150, and resistor 160). After the initial current peak, the current through the resistor 160 exponentially decreases as the capacitors 143 and 145 are charged.

Therefore, in the continuity test the initial voltage peak at the resistor 160 is measured by the measurement circuit 128. The initial voltage peak at the resistor 160 is proportional to the impedance of the lead assembly 106. The measurement circuit 128 can use the magnitude of the initial voltage peak to quantify the impedance of the lead assembly 106 as, for example, low (normal) impedance, high impedance (faulty condition), or open circuit (faulty condition). In certain embodiments, the measurement circuit 128 may be pre-programmed with known ranges for low impedance, high impedance, or an open circuit. The measurement circuit 128 may then use these pre-programmed ranges to classify the detected voltage. In further embodiments, the measurement circuit 128 may use a look-up table to classify the impedance as low, high, or an open circuit condition.

As noted above, the diagnostic and adaptive circuitry 120 is configured to perform adaptive functions based on the results of a diagnostic test. In the example of FIG. 1E, the detection of low impedance indicates a normal condition such that no corrective action may be required. If high impedance is detected (i.e., there is an increase of the impedance of the power/data transmission line), then the level at which power and/or data is transmitted through the electrical lead assembly 106 can be automatically increased in order to compensate for the power losses resulting from the increased impedance. The power loss compensation may be limited to a level defined by the maximum output power of the power and data output circuit 117.

As noted, the continuity test may determine that an open circuit exists in the electrical lead assembly 106. When an open circuit is detected, the diagnostic and adaptive circuitry 120 can be configured to automatically terminate the current flow through the electrical lead assembly 106 to prevent further damage to the device (i.e., secondary module 104).

A third type of diagnostic test may be performed to detect low impedance (indicating a short circuit) between either of the wires 140 and 142 inside of the electrical lead assembly 106 and the external electrode 122. This test, sometimes referred to herein as an "external leakage current test," evaluates the electrical insulation of the wires 140 and 142 to determine if current is leaking from the electrical lead assembly 106 into the recipient's body (i.e., the surrounding tissue and/or body fluid). In an external leakage current test, each of the wires 140 and 142 is tested separately. As such, FIG. 1F illustrates the configuration to perform the external leakage current test for wire 140, while FIG. 1G illustrates the configuration to perform external leakage current test for wire 142.

Figure 1F:
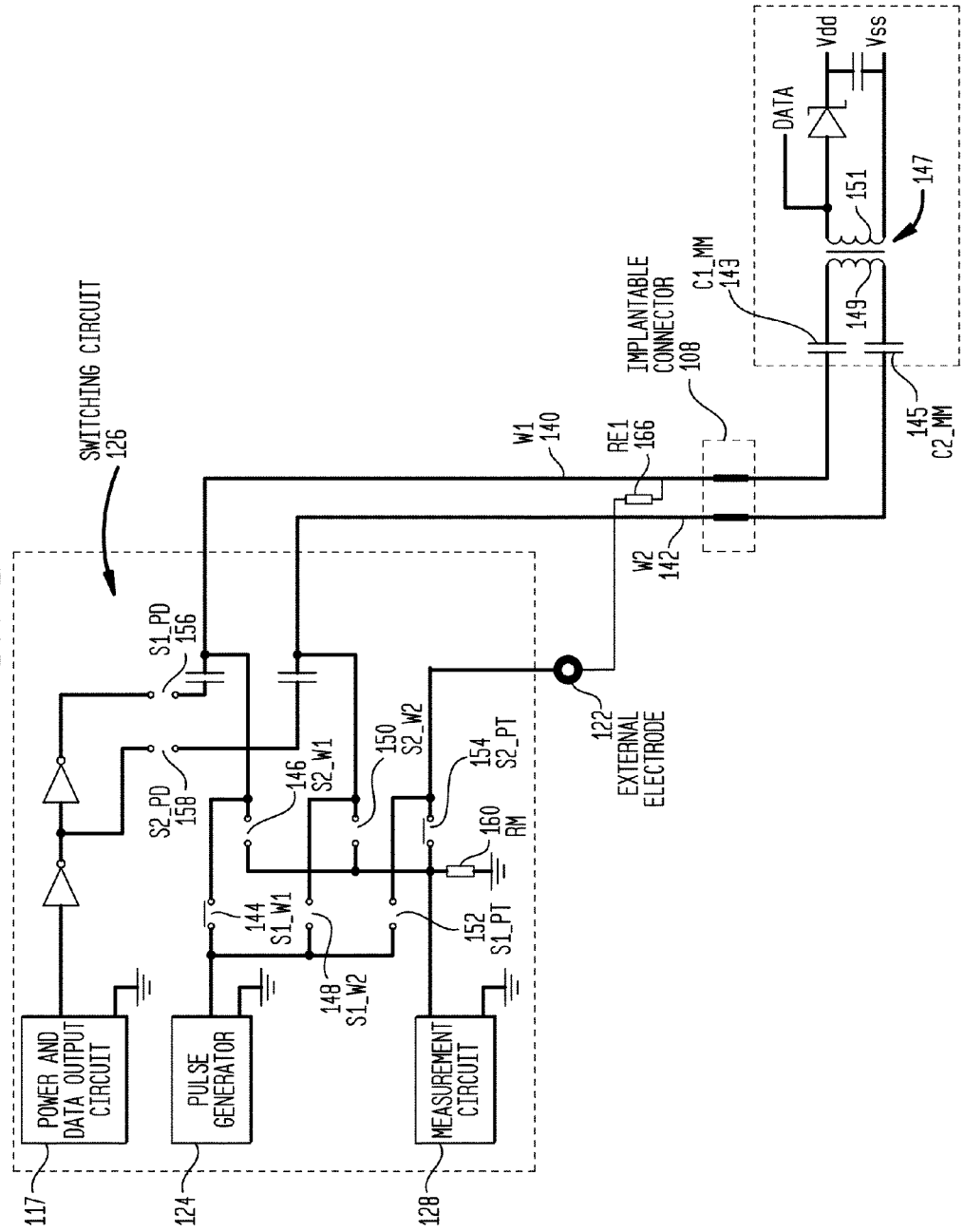
FIG. 1F is a schematic circuit diagram illustrating a configuration for diagnostic and adaptive circuitry in accordance with embodiments presented herein.
Figure 16:
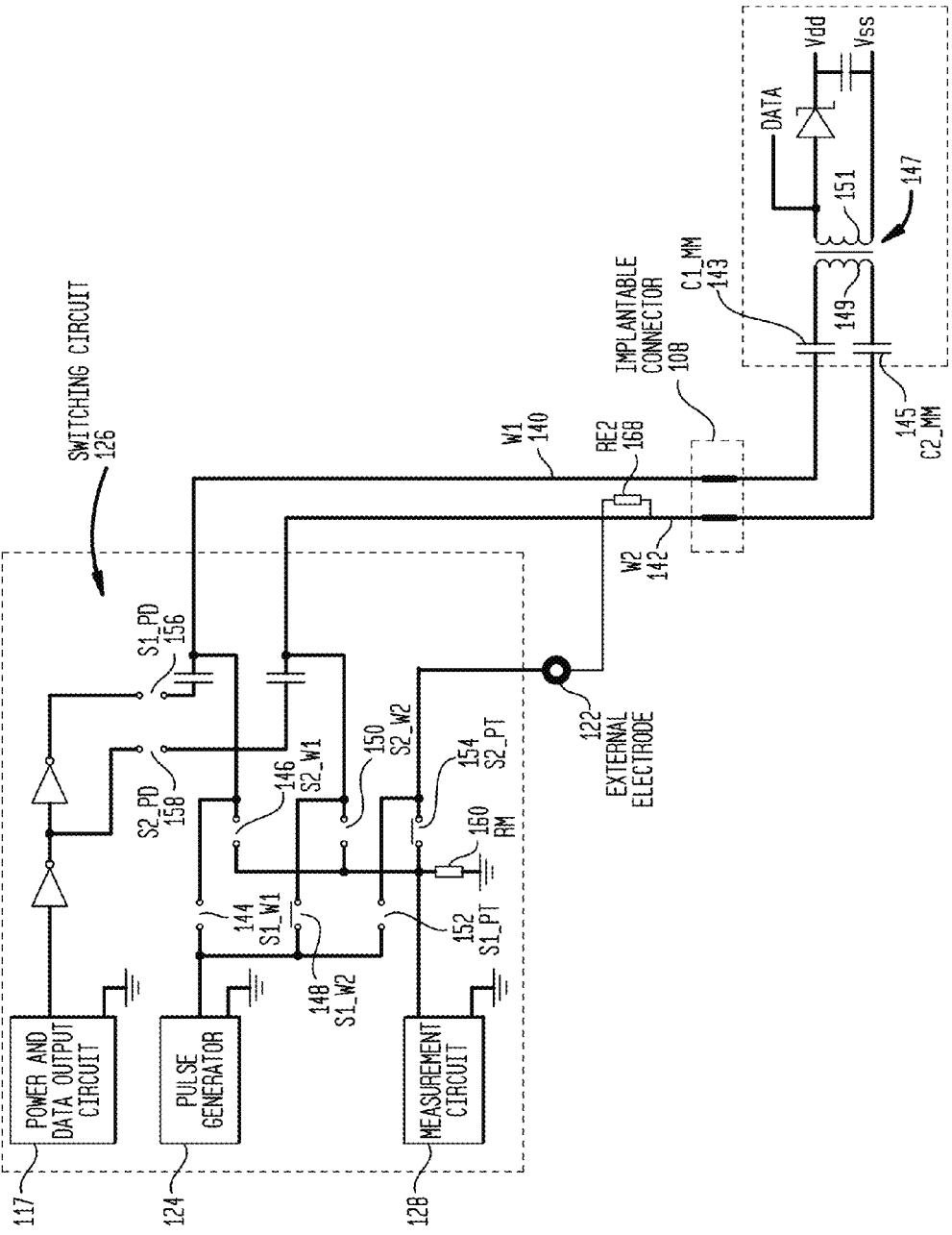

FIG. 1F illustrates a resistor 166 (RE1) within electrical lead assembly 106. The resistor 166 shown in FIG. 1F is not an actual resistor, but instead represents the impedance between the wire 140 and the external electrode 122. Similarly, FIG. 1G illustrates a resistor 168 (RE2) within electrical lead assembly 106. Again, the resistor 168 shown in FIG. 1G is not an actual resistor, but instead represents the impedance between the wire 142 and the external electrode 122.

To perform the leakage current test of wire 140 (i.e., measure the leakage current from wire 140 to the recipient's tissue outside of the lead assembly 106), a voltage pulse is applied to the wire 140 and the external electrode 122 through the measurement resistor 160. If there is no leakage current path between wire 140 and the external electrode 122 (i.e., RE1=∞), then there will be no current flow between the wire 140 and the external electrode 122. As such, the voltage over the measurement resistor 160 will be zero. If there is a leakage current path between the wire 140 and the external electrode 122, then there will be a leakage current flow through RE1 (i.e., through switch 144, wire 140, the recipient's tissue (RE1), external electrode 122, switch 154, and measurement resistor 160 to ground) resulting in a voltage drop over the measurement resistor 160. The voltage across the measurement resistor 160, measured at the end of the voltage pulse by the measurement circuit 128, is proportional to the amplitude of the leakage current between wire 140 and the external electrode 122. Therefore, the measurement circuit 128 can use the voltage level measured at the end of the pulse to quantify the leakage current between the wire 140 and the external electrode 122. That is, the measurement circuit 128 is not only configured to detect the presence of current leakage between the wire 140 and the external electrode 122, but rather may also be configured to determine a magnitude of the current leakage.

As noted above, the diagnostic and adaptive circuitry 120 is configured to perform adaptive functions based on the results of a diagnostic test. In the example of FIG. 1F, the detection of a leakage current between the wire 140 and the external electrode 122 indicates that there is a deterioration of the electrical insulation of the wire 140. As a result, the diagnostic and adaptive circuitry 120 can be configured to automatically limit or terminate the current flow through the electrical lead assembly 106 to prevent tissue damage resulting from the current leak. The diagnostic and adaptive circuitry 120 may also be configured to transmit the results of the external leakage current test to the external device (e.g., external processor, remote control, clinician equipment, etc.) via the telemetry circuit 112 and the implantable coil 119. The telemetry circuit 112 may be configured to transmit, for example, an indication that a current leakage has been detected, an indication of the magnitude of the current leakage, and/or an indication of the corrective action taken by the diagnostic and adaptive circuitry 120. The transmission by the telemetry circuit 112 may occur in real-time (i.e., if an external device is present) or the transition may occur at a later time. As such, the diagnostic and adaptive circuitry 120 may have the ability to temporarily store testing results for subsequent transmission/upload to an external device.

To perform the leakage current test of wire 142 (i.e., measure the leakage current from wire 142 to the recipient's tissue outside of the lead assembly 106), a voltage pulse is applied to the wire 142 and the external electrode 122 through the measurement resistor 160. If there is no leakage current path between wire 142 and the external electrode 122 (i.e., RE2=∞), then there will be no current flow between the wire 142 and the external electrode 122. As such, the voltage over the measurement resistor 160 will be zero. If there is a leakage current path between the wire 142 and the external electrode 122, then there will be a leakage current flow through RE2 (i.e., through switch 148, wire 142, the recipient's tissue (RE2), external electrode 122, switch 154, and measurement resistor 160 to ground) resulting in a voltage drop over the measurement resistor 160. The voltage across the measurement resistor 160, measured at the end of the voltage pulse by the measurement circuit 128, is proportional to the amplitude of the leakage current between wire 142 and the external electrode 122. Therefore, the measurement circuit 128 can use the voltage level measured at the end of the pulse to quantify the leakage current between the wire 142 and the external electrode 122. That is, the measurement circuit 128 is not only configured to detect the presence of current leakage between the wire 142 and the external electrode 122, but rather may also be configured to determine a magnitude of the current leakage.

In operation, switches 146, 150, and 152 may be used to reverse the direction of the leakage current through the leakage path. When current leakage is detected between one of the wires 140 or 142 and the external electrode 122, the reverse direction of the leakage current through the leakage path is needed in order to balance the charge delivered and eliminate electrode polarization effect in the recipient's tissue that results when the leakage current flows through the body. It is to be appreciated that the reverse of the test/leakage current flow may be used for all tests (internal leakage, continuity and external leakage), but it is particularly important for the external leakage test.

As noted above, the diagnostic and adaptive circuitry 120 is configured to perform adaptive functions based on the results of a diagnostic test. In the example of FIG. 1G, the detection of a leakage current between the wire 142 and the external electrode 122 indicates that there is a deterioration of the electrical insulation of the wire 142. As a result, the diagnostic and adaptive circuitry 120 can be configured to automatically limit or terminate the current flow through the electrical lead assembly 106 to prevent tissue damage resulting from the current leak. The diagnostic and adaptive circuitry 120 may also be configured to transmit the results of the external leakage current test to the external device (e.g., external processor, remote control, clinician equipment, etc.) via the telemetry circuit 112 and the implantable coil 119. The telemetry circuit 112 may be configured to transmit, for example, an indication that a current leakage has been detected, an indication of the magnitude of the current leakage, and/or an indication of the corrective action taken by the diagnostic and adaptive circuitry 120. The transmission by the telemetry circuit 112 may occur in real-time (i.e., if an external device is present) or the transition may occur at a later time. As such, the diagnostic and adaptive circuitry 120 may have the ability to temporarily store testing results for subsequent transmission/upload to an external device.

As noted above, FIGS. 1A-1G illustrate the use of an implantable connector 108 in the lead assembly 106. It is to be appreciated that the use of an implantable connector is merely illustrative. In other embodiments, the electrical link between the implantable modules can be direct (i.e., no implantable connector).

Additionally, FIGS. 1A-1G illustrate an embodiment where the diagnostic and adaptive circuitry 120 is part of a cochlear implant. It is to be appreciated that the diagnostic and adaptive circuitry may be used in other implantable hearing prostheses having a main module and a secondary module. For example, in one alternative arrangement the embodiments of FIGS. 1A-1G may be used as part of an auditory brainstem implant. An auditory brainstem implant may have substantially the same configuration as shown in FIGS.

1A-1G except that the stimulating assembly 138 is configured to be implanted in the recipient's brainstem rather than the cochlea.

FIG. 2A is a block diagram of another implantable hearing prosthesis that includes diagnostic and adaptive circuitry in accordance with embodiments presented herein. In the example of FIG. 2A, the implantable hearing prosthesis is a cochlear implant 200 that includes a stimulator module (main module) 202 and a physically separate implantable microphone module 205. The stimulator module 202 and implantable microphone module 205 are each hermetically sealed packages that are electrically connected by an electrical lead assembly (cable) 206.

The stimulator module 202 includes a hermetically sealed housing 230. Disposed in the housing 230 is a decoder and controller 231 (referred to herein simply as controller 231), a telemetry circuit 232, a power supply 213, a battery 214, a battery charging circuit 215, a sound processor 216, a power and data interface 234, a data interface 203, and a current source and switching circuit 235 (referred to herein as stimulator 235). An extra-cochlear electrode (ECE) 236, stimulating assembly lead 237, and an implantable coil (antenna) 239 are each connected to one or more components within the housing 230 via respective feedthroughs. For ease of illustration, the feedthroughs have been omitted from the drawings. The stimulating assembly lead 237 is connected to a stimulating assembly 238 that is configured to be implanted within a recipient's cochlea.

It is be appreciated that in certain embodiments there may be two extra-cochlear electrodes. For simplicity, only one extra-cochlear electrode is shown. In one specific example, in addition to ECE 236, the housing 230 may be a titanium member that operates as a second extra-cochlear electrode.

The stimulator module 202 also includes a pulse generator 224, a switching circuit 226, and a measurement circuit 228. The pulse generator 224, the switching circuit 226, and the measurement circuit 228 are disposed within the housing 230. The extra-cochlear electrode 236, switching circuit 226, pulse generator 224, measurement circuit 228, telemetry circuit 212, and controller 231 collectively form diagnostic and adaptive circuitry 220. As described further below, the switching circuit 226 is configured to switch/select between a stimulation operational mode (i.e., a mode during which data and/or power is supplied to and/or where data is received from the implantable microphone module 205) and a diagnostic operational mode (i.e., a mode during which testing and adaptive operations are performed). Additionally, the pulse generator 224 is configured to source/generate test pulses during the diagnostic operational mode and the measurement circuit 228 is configured to measure the voltage response of the electrical lead assembly 206 to test pulses. The telemetry circuit 232 is configured to supply test results and/or indications of corrective actions performed to an external device that is part of, or operates in conjunction with, the cochlear implant 200. The controller 231 is configured to control/drive the other components of the diagnostic and adaptive circuitry 220 as well as the other components of the stimulator module 202.

The microphone module 205 includes a hermetically sealed housing 210 in which a power and data interface 276 is disposed. An implantable microphone 218 may be partially disposed in the housing 210 or may be positioned external to the housing 210 and connected to components within the housing via a feedthrough.

As noted, the stimulator module 202 is connected to the microphone module 205 via the electrical lead assembly 206. In the example of FIG. 2A, the electrical lead assembly 206 is a four-wire power/data link (i.e., two pairs of wires). A first pair of wires, referred to as wire pair 270 or data link 270, is used to carry data signals from the microphone module 205 to the stimulator module 202. Wire pair 270 includes a first wire 272 (W1_D) and a second wire 274 (W2_D) and forms a two-wire pair. The second pair of wires, sometimes referred to herein as wire pair 280 or power and data link 280, is used to carry power and data from the stimulator module 202 to the microphone module 205. Wire pair 280 includes a first wire 282 (W1_PD) and a second wire 284 (W2_PD) that form a two-wire pair.

In operation, the implantable coil 239 is configured to receive power and/or data from an external device that is part of, or operates in conjunction with, the cochlear implant 200. The received power may be used to recharge battery 214, while the received data may be processed by the sound processor 216. That is, the sound processor 216 is configured to use the data received via the implantable coil 239 and/or data received from the implantable microphone module 205 to generate electrical signals that represent received sound. These electrical signals are used by the stimulator 235 to generate a series of stimulation signals (electrical stimulation pukes). The stimulation pulses, when delivered to the recipient via the stimulating assembly 238, evoke perception of a received sound. In this way, cochlear implant 200 stimulates the recipient's auditory nerve cells, bypassing absent or defective hair cells that normally transduce acoustic vibrations into neural activity.

The diagnostic and adaptive circuitry 220 is configured to execute testing and adaptive (corrective) functions to test the integrity of the electrical lead assembly 206 and to automatically adjust the parameters and/or conditions of the power/data transmission in order to, for example, prevent high (short circuit) currents or to compensate a loss of power due to increased (high) impedance of the four-wire link. The diagnostic and self-adjustment (adaptive) functions can be run automatically every time when the cochlear implant 200 is turned on, at periodic intervals during operation, in response to a received command, etc.

Figure 2B:
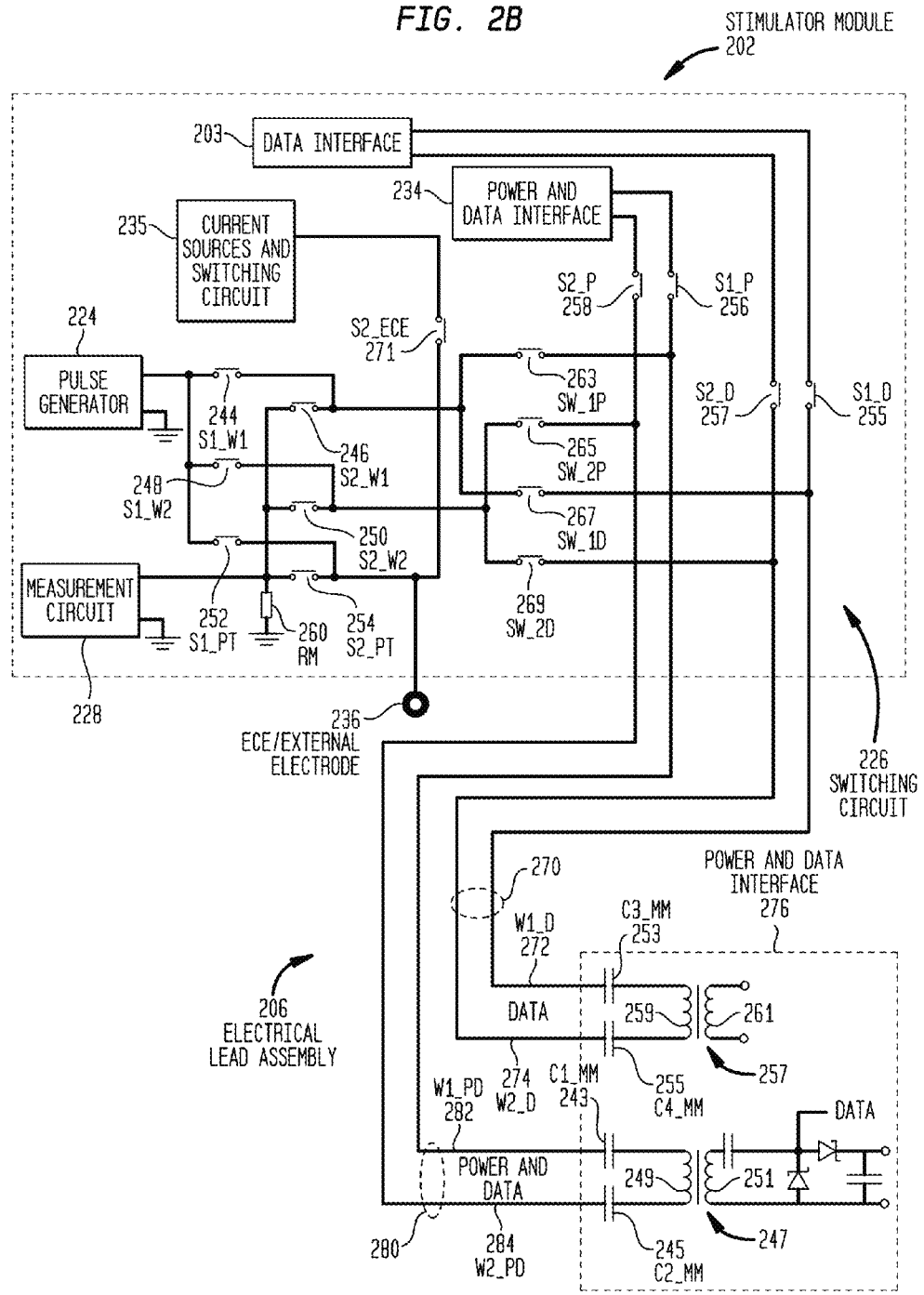
FIG. 2B is a schematic circuit diagram illustrating further details of an electrical lead assembly, microphone module, and diagnostic and adaptive circuitry in accordance with embodiments presented herein.

FIG. 2B illustrates further details of the power and data interface 276 of the microphone module 205 and switching circuit 226. As shown, power and data interface 276 of FIG. 2B includes two transformer coupled interfaces, one interface for the wire pair 270 and one interface for the wire pair 280. More specifically, referring first to wire pair 280, wire 282 terminates at a capacitor 243 (C1_MM), while wire 284 terminates at a capacitor 245 (C2_MM). Capacitors 243 and 245 are coupled to a primary coil 249 of a transformer 247. Transformer 247 also comprises a secondary coil 251.

Referring next to wire pair 270, wire 272 terminates at a capacitor 253 (C3_MM), while wire 274 terminates at a capacitor 255 (C2_MM). Capacitors 253 and 255 are coupled to a secondary coil 259 of a transformer 257. Transformer 257 also comprises a primary coil 261.

It is to be appreciated that the transformer coupled arrangement for power and data interface 276 shown in FIG. 2B is merely illustrative and that other arrangements are possible. For example, in alternative arrangement the interface for wire pair 280 may be replaced with a capacitor coupled interface similar to the capacitor coupled interface shown in FIG. 1C. Merely for ease of illustration, embodiments are generally illustrated herein in use with a transformer coupled interface for wire pair 280.

Returning to the example of FIG. 2B, the switching circuit 226 includes a number of switches that can be selectively activated (closed) to enable the diagnostic and/or adaptive functions of the diagnostic and adaptive circuitry 220. The switching circuit 226 includes a switch 263 (SW_1P) associated with wire 282 (W1_PD) of the wire pair 280, a switch 265 (SW_2P) associated with wire 284 (W2_PD) of the wire pair 280, a switch 267 (SW_1D) associated with wire 272 (W1_D) of wire pair 270, and switch 269 (SW_2D) associated with wire 274 (W2_D) of wire pair 270. The switching circuit 126 also comprises switches 244 (S1_W1) 246 (S2_W1) that are associated with wires 282 (W1_PD) and 272 (W1_D) and switches 248 (S1_W2) and a switch 250 (S2_W2) that are associated with wires 284 (W2_PD) and 274 (W2_D). Furthermore, switching circuit 126 comprises switch 252 (S1_Pt), switch 254 (S2_Pt), and switch 271 (S2_ECE) that are associated with the ECE 236. The ECE 236 is an electrode that is in contact with the body and that is used for stimulation as well as to detect/measure leakage currents from W1_PD or W2_PD or W1_D or W2_D into the recipient's tissue.

Switching circuit 236 further comprises switches 256 (S1_P) and 258 (S2_P) that are associated with the power and data interface 234 as well as switches 255 (S1_D) and 257 (S2_D) are switches associated with the data interface 203. Switches 256 and 258 are configured to connect the power and data interface 234 to wires 282 and 284, respectively, and switches 255 and 257 are configured to connect the data interface 203 to the wires 272 and 274, respectively.

During the stimulation operational mode, power and data signals are applied to the power and data link 280 (wires 282 and 284) through switches 256 and 258 in order to provide power and data to the microphone module 205. Similarly, a data signal may be transmitted from the microphone module 205 to the stimulator module through two-wire link 270 (wires 272 and 274) and switches 255 and 257. Additionally, the ECE 236 is connected to the stimulator 235 through switch 271.

During the diagnostic operational mode, the switching circuit 226 may have a number of different configurations/arrangements depending on the diagnostic test that is performed. However, in general, during the diagnostic operation mode the power and data interface 234 and the data interface 203 are disconnected from the lead assembly 206 (i.e., switches 256, 258, 255, and 257 are open). Additionally, the ECE 236 is disconnected form the stimulator 235 (i.e., switch 271 is open). FIGS. 2C-2F illustrate the configurations of switching circuit 226 during different diagnostic tests.

A first type of diagnostic test may be performed to detect low impedance (indicating a short circuit) between the wires 282 and 284 of the wire pair 280 within the electrical lead assembly 206 or to detect low impedance between the wires 272 and 274 of the wire pair 270 within the electrical lead assembly 206. These type of tests, sometimes referred to herein as an "internal leakage current tests," evaluate the electrical insulation of the wires to determine if a short circuit is present between the wires within a wire pair. The configuration of switching circuit 226 to perform the internal leakage current test for wire pair 280 is shown in FIG. 2C, while the configuration of switching circuit 226 to perform the internal leakage current test for wire pair 270 is shown in FIG. 2D.

Figure 2C:
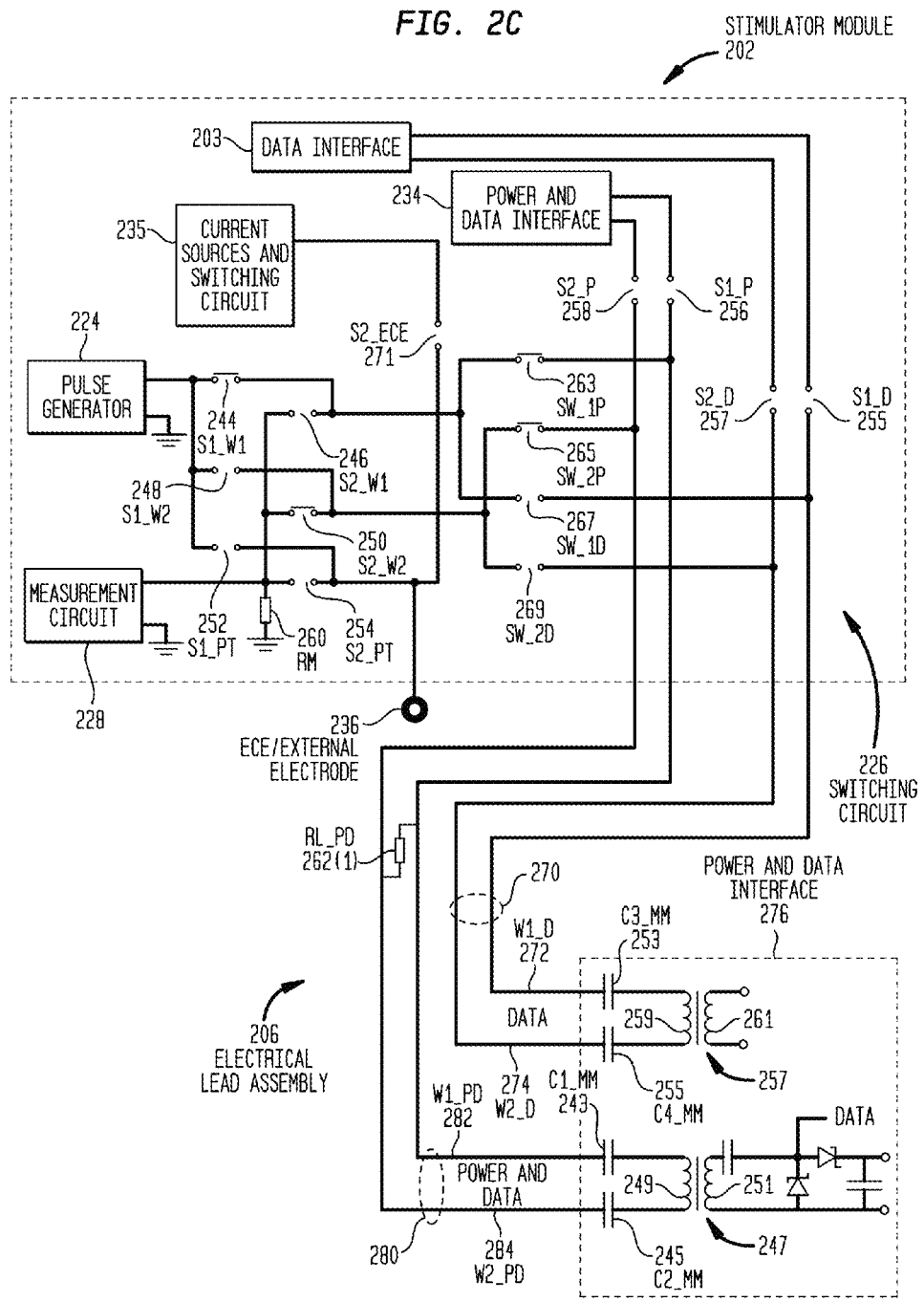
FIG. 2C is a schematic circuit diagram illustrating a configuration for diagnostic and adaptive circuitry in accordance with embodiments presented herein.

Referring first to FIG. 2C, a resistor 262(1) (RL_PD) is shown within electrical lead assembly 206. The resistor 262 (1) shown in FIG. 2C is not an actual resistor, but instead it represents the impedance between the two wires 282 and 284. To perform the internal leakage current test (i.e., measure the leakage current between the wires 282 and 284), a long duration voltage pulse is applied to the wires 282 and 284 of the implantable connector through the measurement resistor 260 (RM). Initially, the current flows from the pulse generator 224 through switches 244 and 263 along wire 282 of the power and data link 280, through capacitor 243 through the primary coil 249 of transformer 247. The current returns from the transformer 247 through the capacitor 245, along wire 284, through switches 265 and 250, and through the resistor 260 to ground.

The current through capacitors 243 and 245 and primary coil 249 exponentially decreases as the capacitors 243 and 245 are charging. When the capacitors 243 and 245 are completely charged, then the current flow through the capacitors 243 and 245 and the primary coil 249 of the transformer 247 will cease. If there is no leakage current path between the wires 282 and 284 (i.e., RL_PD=∞), then there will be no current flow after the capacitors 243 and 245 are charged. As such, the voltage over the resistor 260, which is measured by the measurement circuit 228 after the capacitors 243 and 245 have charged, will be zero. If there is a leakage current path between the wires 282 and 284, then there will be a leakage current flow resulting in a voltage drop over the resistor 260.

The voltage across the resistor 260 is measured by the measurement circuit 228 at the end of the voltage pulse initiated by pulse generator 224. The voltage across the resistor 260 is also proportional to the amplitude of the leakage current between the wires 282 and 284. Therefore, the measurement circuit 228 can use the voltage level measured at the end of the pulse to quantify the leakage current between the wires 282 and 284. That is, the measurement circuit 228 is not only configured to detect the presence of current leakage between the wires 282 and 284, but rather may also be configured to determine a magnitude of the current leakage.

Referring next to FIG. 2D, a resistor 262(2) (RL_D) is shown within electrical lead assembly 206. The resistor 262 (2) shown in FIG. 2D is not an actual resistor, but instead it represents the impedance between the two wires 272 and 274. To perform the internal leakage current test (i.e., measure the leakage current between the wires 272 and 274), a long duration voltage pulse is applied to the wires 272 and 274 of the implantable connector through the measurement resistor 260 (RM). Initially the current flows from the pulse generator 224 through switches 244 and 267 along wire 272 of the data link 270, through capacitor 253, to the secondary coil 259 of the transformer 257. The current flows from the secondary coil 259 through the capacitor 255, along wire 274, through switches 269 and 250, and through the resistor 260 to ground.

Similar to the embodiment of FIG. 2C, the current through capacitors 253 and 255 and secondary coil 259 exponentially decreases as the capacitors 253 and 255 are charging. When the capacitors 253 and 255 are completely charged, then the current flow through the capacitors 253 and 255 and the secondary coil 259 of the transformer 257 will cease. If there is no leakage current path between the wires 272 and 274 (i.e., RL_D=∞), then there will be no current flow after the capacitors 253 and 255 are charged. As such, the voltage over the resistor 260, which is measured by the measurement circuit 228 after the capacitors 253 and 255 have charged, will be zero. If there is a leakage current path between the wires 272 and 274, then there will be a leakage current flow resulting in a voltage drop over the resistor 260.

The voltage across the resistor 260 is measured by the measurement circuit 228 at the end of the voltage pulse initiated by pulse generator 224. The voltage across the resistor 260 is also proportional to the amplitude of the leakage current between the wires 272 and 274. Therefore, the measurement circuit 228 can use the voltage level measured at the end of the pulse to quantify the leakage current between the wires 272 and 274. That is, the measurement circuit 228 is not only configured to detect the presence of current leakage between the wires 272 and 274, but rather may also be configured to determine a magnitude of the current leakage.

As noted above, the diagnostic and adaptive circuitry 220 is configured to perform adaptive functions based on the results of a diagnostic test. In the examples of FIGS. 2C and 2D, the detection of low impedance between the wires within a wire pair indicates that there is a deterioration of the electrical insulation between the wires. As a result, the diagnostic and adaptive circuitry 220 can be configured to automatically limit or terminate the current flow through the electrical lead assembly 206 to prevent tissue damage resulting from heating of the lead assembly 206 (i.e., resulting from a temperature rise due to a short between two wires). That is, the excessive current consumption (due to the low impedance/short between the wires) can cause overheating of the electronic components (increase of the power dissipation) in module 202, resulting in temperature rise of the module 202. As such, the diagnostic and adaptive circuitry 220 provides high current protection for module 202 and the electrical lead assembly 206. The diagnostic and adaptive circuitry 220 may also be configured to transmit the results of the leakage current test to the external device (e.g., external processor, remote control, clinician equipment, etc.) via the telemetry circuit 232 and the implantable coil 239. The telemetry circuit 232 may be configured to transmit, for example, an indication that a current leakage has been detected, an indication of the magnitude of the current leakage, and/or an indication of the corrective action taken by the diagnostic and adaptive circuitry 220. The transmission by the telemetry circuit 232 may occur in real-time (i.e., if an external device is present) or the transition may occur at a later time. As such, the diagnostic and adaptive circuitry 320 may have the ability to temporarily store testing results for subsequent transmission/upload to an external device.

A second type of diagnostic test may be performed by the diagnostic adaptive circuitry 220 to detect low (normal) impedance, high impedance (faulty condition), or open circuit (faulty condition) at each of the wires 272, 274, 282, and 284. This test is sometimes referred to herein as a "continuity test" and tests the electrical continuity of the wires 272, 274, 282, and 284. The configuration of switching circuit 226 to perform the continuity test of wires 282 and 284 is shown in FIG. 2E, while the configuration of switching circuit 226 to perform the continuity test of wires 272 and 274 is shown in FIG. 2F.

Referring first to FIG. 2E, a resistor 264(1) (RS_PD) is shown within electrical lead assembly 206. The resistor 264(1) shown in FIG. 2E is not an actual resistor, but instead represents the impedance along the electrical path defined by the wires 282 and 284. To perform the continuity test of wires 282 and 284, a voltage pulse is applied to the wires 282 and 284 of the power and data link 280 through the measurement resistor 260. Initially the current flows from the pulse generator 224 through switches 244 and 263 along wire 282 of the power and data link 280, through capacitor 243 through the primary coil 249 of transformer 247. The current returns from the primary coil 249 of transformer 247 through the capacitor 245, along wire 284, through switches 265 and 250, and through the resistor 260 to ground.

The initial amplitude of the current (i.e., the initial current peak), measured at resistor 260 by measurement circuit 228, is proportional to the impedance of the current path (i.e., the path defined by switch 244, switch 263, wire 282, capacitor 243, coil 249, capacitor 245, wire 284, switch 265, switch 250, and resistor 260). After the initial current peak, the current through the resistor 260 exponentially decreases as the capacitors 243 and 245 are charged.

Therefore, in the continuity test of FIG. 2E, the initial voltage peak at the resistor 260 is measured by the measurement circuit 228. The initial voltage peak at the resistor 260 is proportional to the impedance of power-data link 280. The measurement circuit 228 can use the magnitude of the initial voltage peak to quantify the impedance of the power-data link 280 as, for example, low (normal) impedance, high impedance (faulty condition), or open circuit (faulty condition). In certain embodiments, the measurement circuit 228 may be pre-programmed with known ranges for low impedance, high impedance, or an open circuit. The measurement circuit 228 may then use these pre-programmed ranges to classify the detected voltage. In further embodiments, the measurement circuit 228 may use a look-up table to classify the impedance as low, high, or an open circuit condition.

Referring next to FIG. 2F, a resistor 264(2) (RS_D) is shown within electrical lead assembly 206. The resistor 264(2) shown in FIG. 2F is not an actual resistor, but instead represents the impedance along the electrical path defined by the wires 272 and 274. To perform the continuity test of wires 272 and 274, a voltage pulse is applied to the wires 272 and 274 of the data link 270 through the measurement resistor 260. Initially the current flows from the pulse generator 224 through switches 244 and 267 along wire 272 of the data link 270, through capacitor 253 through the secondary coil 259 of transformer 257. The current returns from the transformer 257 through the capacitor 255, along wire 274, through switches 269 and 250, and through the resistor 260 to ground.

The initial amplitude of the current (i.e., the initial current peak), measured at resistor 260 by measurement circuit 228, is proportional to the impedance of the current path (i.e., the path defined by switch 244, switch 267, wire 272, capacitor 253, coil 259, capacitor 255, wire 274, switch 269, switch 250, and resistor 260). After the initial current peak, the current through the resistor 260 exponentially decreases as the capacitors 253 and 255 are charged.

Therefore, in the continuity test of FIG. 2F, the initial voltage peak at the resistor 260 is measured by the measurement circuit 228. The initial voltage peak at the resistor 260 is proportional to the impedance of data link 270. The measurement circuit 228 can use the magnitude of the initial voltage peak to quantify the impedance of the data link 270 as, for example, low (normal) impedance, high impedance (faulty condition), or open circuit (faulty condition). In certain embodiments, the measurement circuit 228 may be pre-programmed with known ranges for low impedance, high impedance, or an open circuit. The measurement circuit 228 may then use these pre-programmed ranges to classify the detected voltage. In further embodiments, the measurement circuit 228 may use a look-up table to classify the impedance as low, high, or an open circuit condition.

As noted above, the diagnostic and adaptive circuitry 220 is configured to perform adaptive functions based on the results of a diagnostic test. In the examples of FIGS. 2E and 2F, the detection of low impedance indicates a normal condition such that no corrective action may be required. If high impedance is detected (i.e., there is an increase of the impedance of the power/data transmission line), then the level at which power and/or data is transmitted through the power-data link 280 and/or the data link 270 can be automatically increased in order to compensate for the power losses resulting from the increased impedance.

As noted, the continuity tests may determine that an open circuit exists in the electrical lead assembly 206. When an open circuit is detected, the diagnostic and adaptive circuitry 220 can be configured to automatically terminate the current flow through the power-data link 280 and/or the data link 270 to prevent dame to the device (i.e., stimulator module 202).

A third type of diagnostic test may be performed to detect low impedance (indicating a short circuit) between any of the wires 272, 274, 282, and 284 inside of the electrical lead assembly 206 and the external environment (i.e., the recipient's tissue). This type of test, sometimes referred to herein as an "external leakage current test," evaluates the electrical insulation of the wires 272, 274, 282, and 284 to determine if current is leaking from the electrical lead assembly 206 into the recipient's body (i.e., the surrounding tissue and/or body fluid). In an external leakage current test, each of the wires 272, 274, 282, and 284 is tested separately. For brevity, the configurations of switching circuit 226 for performance of the external leakage current tests for each of the wires 272, 274, 282, and 284 have been omitted. However, each of the external leakage current tests for wires 272, 274, 282, and 284 are described fully below with reference to FIG. 2B.

First, to perform the leakage current test of wire 282 (i.e., measure the leakage current from wire 282 to the recipient's tissue outside of the lead assembly 206), a voltage pulse is applied to the wire 282 and the ECE 236 through the measurement resistor 260. If there is no leakage current path between wire 282 and the ECE 236, then there will be no current flow between the wire 282 and the ECE 236. As such, the voltage over the measurement resistor 260 will be zero. If there is a leakage current path between the wire 282 and the ECE 236, then there will be a leakage current flow through the path (i.e., switch 244, switch 263, wire 282, the recipient's tissue, ECE 236, switch 254, and measurement resistor 260 to ground) resulting in a voltage drop across the measurement resistor 260. The voltage across the measurement resistor 260, measured at the end of the voltage pulse by the measurement circuit 228, is proportional to the amplitude of the leakage current between wire 282 and the ECE 236. Therefore, the measurement circuit 228 can use the voltage level measured at the end of the pulse to quantify the leakage current between the wire 282 and the ECE 236. That is, the measurement circuit 228 is not only configured to detect the presence of current leakage between the wire 282 and the ECE 236, but rather may also be configured to determine a magnitude of the current leakage.

Second, to perform the leakage current test of wire 284 (i.e., measure the leakage current from wire 284 to the recipient's tissue outside of the lead assembly 206), a voltage pulse is applied to the wire 284 and the ECE 236 through the measurement resistor 260. If there is no leakage current path between wire 284 and the ECE 236, then there will be no current flow between the wire 284 and the ECE 236. As such, the voltage over the measurement resistor 260 will be zero. If there is a leakage current path between the wire 284 and the ECE 236, then there will be a leakage current flow through the path (i.e., switch 244, switch 265, wire 284, the recipient's tissue, ECE 236, switch 254, and measurement resistor 260 to ground) resulting in a voltage drop across the measurement resistor 260. The voltage across the measurement resistor 260, measured at the end of the voltage pulse by the measurement circuit 228, is proportional to the amplitude of the leakage current between wire 284 and the ECE 236. Therefore, the measurement circuit 228 can use the voltage level measured at the end of the pulse to quantify the leakage current between the wire 284 and the ECE 236. That is, the measurement circuit 228 is not only configured to detect the presence of current leakage between the wire 284 and the ECE 236, but rather may also be configured to determine a magnitude of the current leakage.

Third, to perform the leakage current test of wire 272 (i.e., measure the leakage current from wire 272 to the recipient's tissue outside of the lead assembly 206), a voltage pulse is applied to the wire 272 and the ECE 236 through the measurement resistor 260. If there is no leakage current path between wire 272 and the ECE 236, then there will be no current flow between the wire 272 and the ECE 236. As such, the voltage over the measurement resistor 260 will be zero. If there is a leakage current path between the wire 272 and the ECE 236, then there will be a leakage current flow through the path (i.e., switch 244, switch 267, wire 272, the recipient's tissue, ECE 236, switch 254, and measurement resistor 260 to ground) resulting in a voltage drop across the measurement resistor 260. The voltage across the measurement resistor 260, measured at the end of the voltage pulse by the measurement circuit 228, is proportional to the amplitude of the leakage current between wire 272 and the ECE 236. Therefore, the measurement circuit 228 can use the voltage level measured at the end of the pulse to quantify the leakage current between the wire 272 and the ECE 236. That is, the measurement circuit 228 is not only configured to detect the presence of current leakage between the wire 272 and the ECE 236, but rather may also be configured to determine a magnitude of the current leakage.

Fourth, to perform the leakage current test of wire 274 (i.e., measure the leakage current from wire 274 to the recipient's tissue outside of the lead assembly 206), a voltage pulse is applied to the wire 274 and the ECE 236 through the measurement resistor 260. If there is no leakage current path between wire 274 and the ECE 236, then there will be no current flow between the wire 274 and the ECE 236. As such, the voltage over the measurement resistor 260 will be zero. If there is a leakage current path between the wire 274 and the ECE 236, then there will be a leakage current flow through the path (i.e., switch 244, switch 269, wire 274, the recipient's tissue, ECE 236, switch 254, and measurement resistor 260 to ground) resulting in a voltage drop across the measurement resistor 260. The voltage across the measurement resistor 260, measured at the end of the voltage pulse by the measurement circuit 228, is proportional to the amplitude of the leakage current between wire 274 and the ECE 236. Therefore, the measurement circuit 228 can use the voltage level measured at the end of the pulse to quantify the leakage current between the wire 274 and the ECE 236. That is, the measurement circuit 228 is not only configured to detect the presence of current leakage between the wire 274 and the ECE 236, but rather may also be configured to determine a magnitude of the current leakage.

As noted above, the diagnostic and adaptive circuitry 220 is configured to perform adaptive functions based on the results of a diagnostic test. In the external leakage current examples, the detection of a leakage current between any of the wires 272, 274, 282, and 284 and the ECE 236 indicates that there is a deterioration of the electrical insulation of the wire. As a result, the diagnostic and adaptive circuitry 220 can be configured to automatically limit or terminate the current flow through the power-data link 280 and/or the data link 270 to prevent tissue damage resulting from the current leak. The diagnostic and adaptive circuitry 220 may also be configured to transmit the results of the external leakage current tests to the external device (e.g., external processor, remote control, clinician equipment, etc.) via the telemetry circuit 232 and the implantable coil 239. The telemetry circuit 232 may be configured to transmit, for example, an indication that a current leakage has been detected, an indication of the magnitude of the current leakage, the wire from which the leakage was detected, and/or an indication of the corrective action taken by the diagnostic and adaptive circuitry 220. The transmission by the telemetry circuit 232 may occur in real-time (i.e., if an external device is present) or the transition may occur at a later time. As such, the diagnostic and adaptive circuitry 220 may have the ability to temporarily store testing results for subsequent transmission/upload to an external device.

In operation, switches 246, 250, and 252 may be used to reverse the direction of the leakage current through the leakage path. When current leakage is detected between one of the wires and the external electrode 236, the reverse direction of the leakage current through the leakage path is needed in order to balance the charge delivered and eliminate electrode polarization effect in the recipient's tissue that results when the leakage current flows through the body. The reverse of the test current flow may be used for all tests (internal leakage, continuity and external leakage), but it is particularly important for the external leakage test.

FIGS. 2A-2F illustrates an embodiment where the diagnostic and adaptive circuitry 220 is part of a cochlear implant. It is to be appreciated that the diagnostic and adaptive circuitry may be used in other implantable hearing prostheses having a stimulator module and a microphone module. For example, in one alternative arrangement the embodiments of FIGS. 2A-2F may be used as part of an auditory brainstem implant. An auditory brainstem implant may have substantially the same configuration as shown in FIGS. 2A-2F except that the stimulating assembly 238 is configured to be implanted in the recipient's brainstem rather than the cochlea.

FIG. 3A is a block diagram of another implantable hearing prosthesis that includes diagnostic and adaptive circuitry in accordance with embodiments presented herein. In the example of FIG. 3A, the implantable hearing prosthesis is a direct acoustic cochlear stimulator 300 that includes a stimulator module (main module) 302 and a physically separate actuator 386. The stimulator module 302 and the actuator 386 are each hermetically sealed packages that are electrically connected by an electrical lead assembly (cable) 306.

The stimulator module 302 includes a hermetically sealed housing 330. Disposed in the housing 330 is a decoder and controller 331 (referred to herein simply as a controller 331), a telemetry circuit 332, a power supply 313, and an actuator driver 308. The stimulator module 302 also includes an external electrode 322, an implantable coil 339, a pulse generator 324, a switching circuit 326, and a measurement circuit 328. The pulse generator 324, the switching circuit 326, and the measurement circuit 328 are disposed within the housing 330. The external electrode 122 is connected to the switching circuit 326 via a feedthrough. The implantable coil 339 is also connected to one or more components within the housing 330 via a feedthrough. For ease of illustration, the feedthroughs in stimulator module 302 have been omitted from the drawings.

The external electrode 322, switching circuit 326, pulse generator 324, measurement circuit 328, telemetry circuit 322, and the controller 331 collectively form diagnostic and adaptive circuitry 320. As described further below, the switching circuit 326 is configured to switch/select between a stimulation operational mode (i.e., a mode during which power is supplied to the actuator 386) and a diagnostic operational mode (i.e., a mode during which testing and adaptive operations are performed). The pulse generator 324 is configured to source/generate test pulses during the diagnostic operational mode, while the measurement circuit 328 is configured to measure the voltage response of the electrical lead assembly 306 to test pulses. The telemetry circuit 332 is configured to supply test results and/or indications of corrective actions performed to an external device (not shown) that is part of, or operates in conjunction with, the direct acoustic cochlear stimulator 300. The controller 331 is configured to control/drive the other components of the diagnostic and adaptive circuitry 320.

In operation, the implantable coil 339 is configured to receive power and/or data from the external device (not shown) that is part of, or operates in conjunction with, the direct acoustic cochlear stimulator 300. The received power may be used to recharge the power supply 313, while the received data may be used by the actuator driver 308. More specifically, the data are coded signals that represent a received sound. The actuator driver 308 is configured to convert these coded signals into drive signals for delivery to the actuator 386 via lead assembly 306. The drive signals cause actuation of the actuator 386 and corresponding actuation of a coupling element 388 that is configured to be attached to the recipient's cochlea (e.g., the oval window, round window, etc.) Actuation of the coupling element 388 creates waves of fluid motion within the recipient's cochlea that evoke perception of the received sound.

As noted, the stimulator module 302 is connected to the actuator 386 via the electrical lead assembly 306. The electrical lead assembly 306 is a two-wire power/data link (i.e., one pair of wires) that is selectively used to carry the coded signals and power to the actuator 386.

The diagnostic and adaptive circuitry 320 is configured to execute testing and adaptive (corrective) functions to test the integrity of the electrical lead assembly 306 and to automatically adjust the parameters and/or conditions of the power/data transmission in order to, for example, prevent high (short circuit) currents or to compensate for a loss of power due to increased (high) impedance of the two-wire link. The diagnostic and adaptive functions can be run automatically every time when the direct acoustic cochlear stimulator 300 is turned on, at periodic intervals during operation, in response to a received command, etc.

Figure 3B:
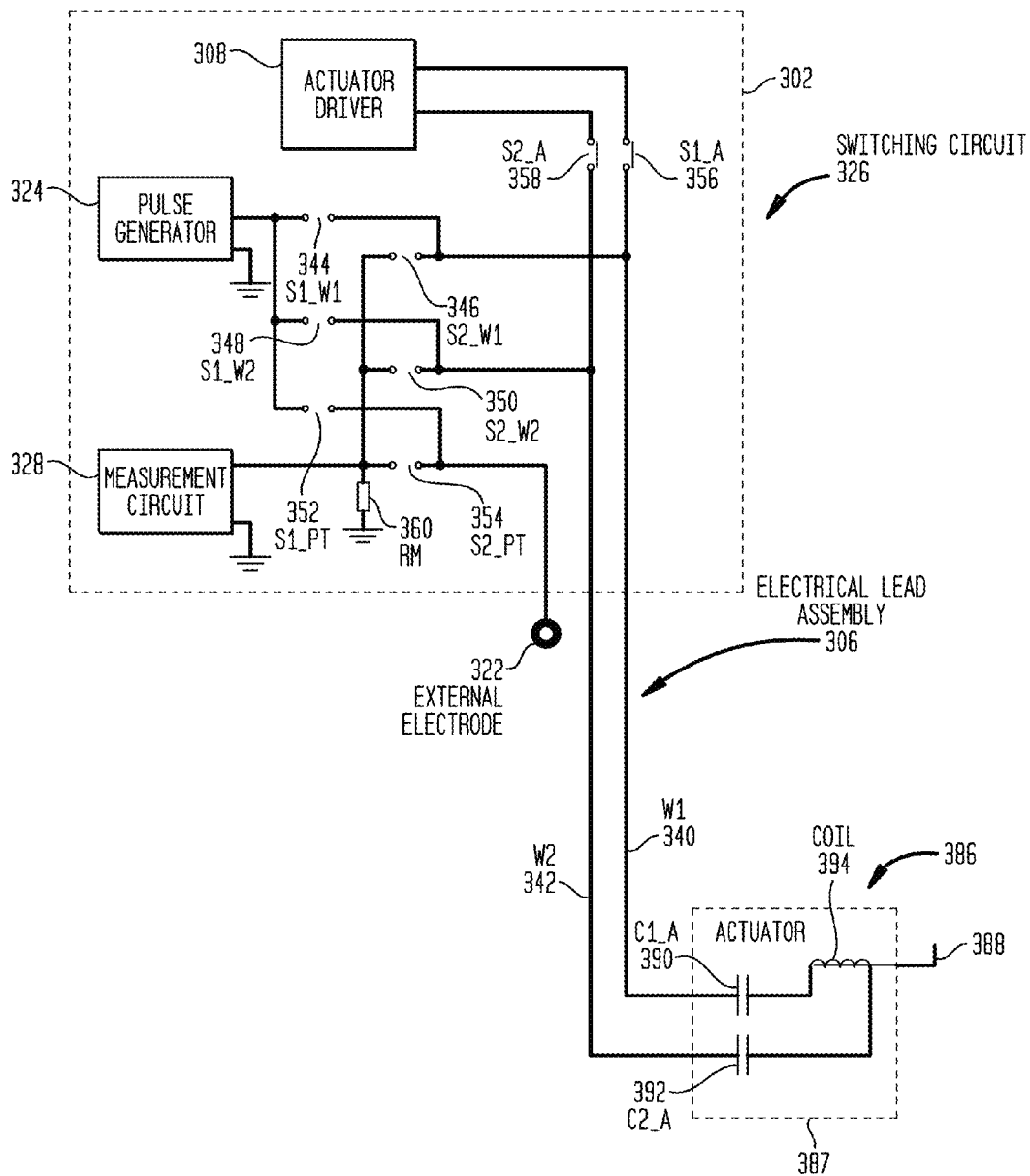
FIG. 3B is a schematic circuit diagram illustrating further details of an electrical lead assembly, mechanical actuator, and diagnostic and adaptive circuitry in accordance with embodiments presented herein.

FIG. 3B is a schematic diagram illustrating further details of the electrical lead assembly 306, the actuator 386, and part of the diagnostic and adaptive circuitry 320. The electrical lead assembly 306 includes a first wire (W1) 340 and a second wire (W2) 342. The electrical lead assembly 306 is sometimes referred to herein as a two-wire link.

In the example of FIG. 3B, the actuator 386 comprises a housing 387 that may be, for example, a titanium case. The actuator 386 also comprises a first capacitor (C1_A) 390, a coil 394, and a second capacitor (C2_A) 392. The coil 394 is used to induce motion of the coupling member 388.

The switching circuit 326 includes a number of switches that can be selectively activated (closed) to enable the diagnostic and/or adaptive functions of the diagnostic and adaptive circuitry 320. First, the switching circuit 326 includes a switch 344 (S1_W1) and a switch 346 (S2_W1) that are associated with wire 340 (W1). Additionally, the switching circuit 326 includes a switch 348 (S1_W2) and a switch 350 (S2_W2) that are associated with wire 342 (W2). Furthermore the switching circuit 326 includes switch 352 (S1_PT) and switch 354 (S2_PT) that are associated with the external electrode 322. As described further below, the external electrode 322 is in contact with the recipient's tissue and/or body fluid and is used to detect/measure leakage current from 340 W1 or 342 W2 to the body.

The switching circuit 326 also includes switch 356 (S1_A) and switch 358 (S2_A) that are associated with the actuator 308. Switch 356 is configured to connect wire 340 to the actuator 308, while the switch 358 is configured to connect the wire 342 to the actuator 308.

During the stimulation operational mode, the switching circuit 326 is configured such that power/data signals are applied to the two-wire link (wires 340, 342) through switches 356 and 358. That is, switches 356 and 358 are closed while the other switches are open so as to disconnect pulse generator 324 and measurement circuit 328 from the two-wire link. During the diagnostic operational mode, the switching circuit 326 may have a number of different configurations/arrangements depending on the diagnostic test that is performed. FIGS. 3C-3H illustrate the configurations of switching circuit 326 during different diagnostic tests.

A first type of diagnostic test may be performed to detect low impedance (indicating a short circuit) between the wires 340 and 342 inside of the electrical lead assembly 306. This type of test, sometimes referred to herein as an "internal leakage current test," evaluates the electrical insulation of the wires 340 and 342 to determine if a short circuit is present between the wires. The configuration of switching circuit 326 to perform the internal leakage current test is shown in FIG. 3C.

Figure 3C:
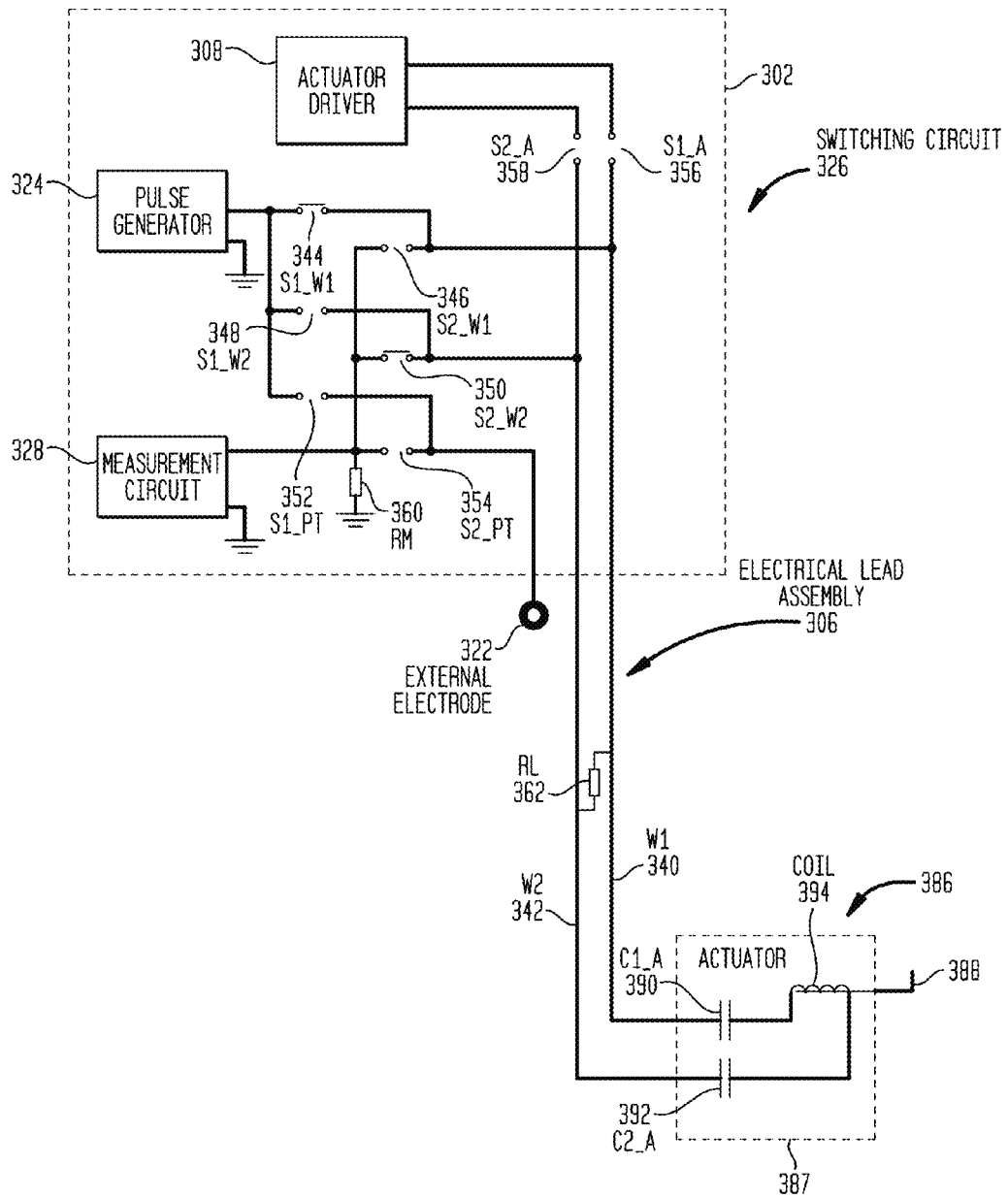
FIG. 3C is a schematic circuit diagram illustrating a configuration for diagnostic and adaptive circuitry in accordance with embodiments presented herein.
Figure 3D:
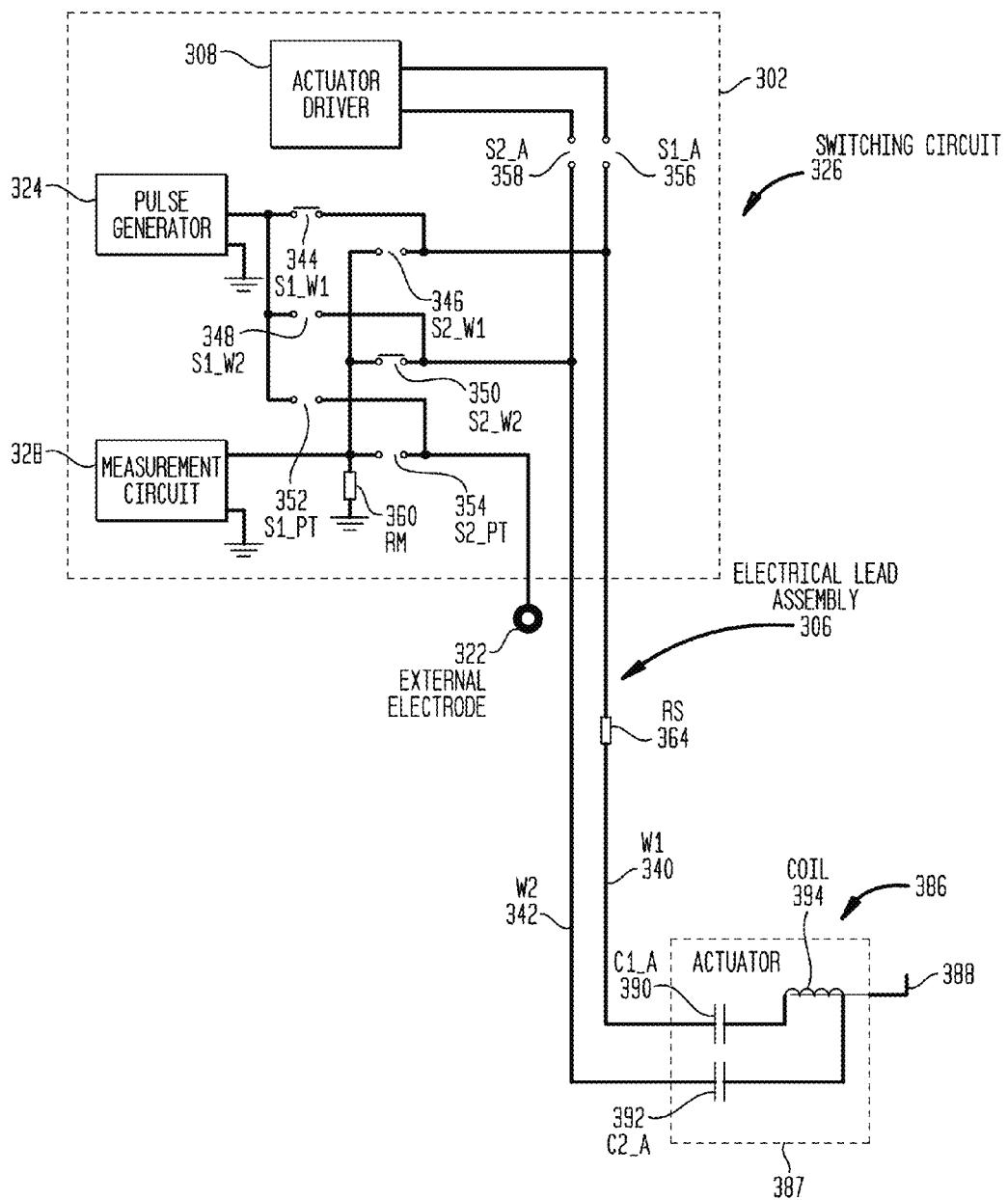
FIG. 3D is a schematic circuit diagram illustrating a configuration for diagnostic and adaptive circuitry in accordance with embodiments presented herein.

FIG. 3C illustrates a resistor 362 (RL) within electrical lead assembly 306. The resistor 362 shown in FIG. 3D is not an actual resistor, but instead it represents the impedance between the two wires 340 and 342. To perform the internal leakage current test (i.e., measure the leakage current between the wires 340 and 342), a long duration voltage pulse is applied to the wires 340 and 342 of the implantable connector through a measurement resistor 360 (RM). Initially, current flows from the pulse generator 324 through switch 344 along wire 340 through capacitor 390 to the 394. The current returns from the coil 394 through capacitor 392, along wire 342, through switch 350, and finally through the resistor 360 to ground.

The current through capacitors 390 and 392 exponentially decreases as the capacitors are charging. When the capacitors 390 and 392 are completely charged, then the current flow through the capacitors and the coil 394 will cease. If there is no leakage current path between the wires 340 and 342 (i.e., RL=∞), then there will be no current flow after the capacitors 390 and 392 are been charged. As such, the voltage over the resistor 360, which is measured by the measurement circuit 328 after the capacitors 390 and 392 have charged, will be zero. If there is a leakage current path between the wires 340 and 342, then there will be a leakage current flow resulting in a measurable voltage drop over the resistor 360.

The voltage across the resistor 360 is measured by the measurement circuit 328 at the end of the voltage pulse initiated by pulse generator 324. The voltage across the resistor 360 is also proportional to the amplitude of the leakage current between the wires 340 and 342. Therefore, the measurement circuit 328 can use the voltage level measured at the end of the pulse to quantify the leakage current between the wires 340 and 342. That is, the measurement circuit 328 is not only configured to detect the presence of current leakage between the wires 340 and 342, but rather may also be configured to determine a magnitude of the current leakage.

As noted above, the diagnostic and adaptive circuitry 320 is configured to perform adaptive functions based on the results of a diagnostic test. In the example of FIG. 3C, the detection of low impedance between the wires 340 and 342 indicates that there is a deterioration of the electrical insulation between the wires. As a result, the diagnostic and adaptive circuitry 320 can be configured to automatically limit or terminate the current flow through the electrical lead assembly 306 to prevent tissue damage resulting from heat released by the lead assembly 306 (i.e., resulting from a temperature rise due to short between the wires). That is, the excessive current consumption (due to the low impedance/short between the wires) can cause overheating of the electronic components (increase of the power dissipation) in module 302, resulting in temperature rise of the module 302. As such, the diagnostic and adaptive circuitry 320 provides high current protection for module 302 and the electrical lead assembly 306. The diagnostic and adaptive circuitry 320 may also be configured to transmit the results of the leakage current test to the external device (e.g., external processor, remote control, clinician equipment, etc.) via the telemetry circuit 332 and the implantable coil 339. The telemetry circuit 332 may be configured to transmit, for example, an indication that a current leakage has been detected, an indication of the magnitude of the current leakage, and/or an indication of the corrective action taken by the diagnostic and adaptive circuitry 320. The transmission by the telemetry circuit 332 may occur in real-time (i.e., if an external device is present) or the transition may occur at a later time. As such, the diagnostic and adaptive circuitry 320 may have the ability to temporarily store testing results for subsequent transmission/upload to an external device.

A second type of diagnostic test may be performed by the diagnostic adaptive circuitry 320 to detect low (normal) impedance, high impedance (faulty condition), or open circuit (faulty condition) at each of the wires 340 or 342. This test is sometimes referred to herein as a "continuity test" and tests the electrical continuity of the wires 340 and 342. The configuration to perform the continuity test is shown in FIG. 3D.

FIG. 3D illustrates a resistor 364 (RS) within electrical lead assembly 306. The resistor 364 shown in FIG. 3D is not an actual resistor, but instead represents the impedance along the electrical path defined by the wires 340 and 342. To perform the continuity test, a voltage pulse is applied to the wires 340 and 342 of the implantable lead assembly through the measurement resistor 360. Initially, current flows from the pulse generator 324 through switch 344, along wire 340, through capacitor 390 to the coil 394. The current returns from the coil 394 through capacitor 392, along wire 342, through switch 350, and through the resistor 360 to ground.

The initial amplitude of the current (i.e., the initial current peak), measured at resistor 360 by measurement circuit 328, is proportional to the impedance of the current path (i.e., the path defined by switch 344, wire 340, capacitor 390, coil 394, capacitor 392, wire 342, switch 350, and measurement resistor 360). After the initial current peak, the current through the resistor 360 exponentially decreases as the capacitors 390 and 392 are charged.

Therefore, in the continuity test the initial voltage peak at the resistor 360 is measured by the measurement circuit 328. The initial voltage peak at the resistor 360 is proportional to the impedance of the lead assembly 306. The measurement circuit 328 can use the magnitude of the initial voltage peak to quantify the impedance of the lead assembly 306 as, for example, low (normal) impedance, high impedance (faulty condition), or open circuit (faulty condition). In certain embodiments, the measurement circuit 328 may be pre-programmed with known ranges for low impedance, high impedance, or an open circuit. The measurement circuit 328 may then use these pre-programmed ranges to classify the detected voltage. In further embodiments, the measurement circuit 328 may use a look-up table to classify the impedance as low, high, or an open circuit condition.

As noted above, the diagnostic and adaptive circuitry 320 is configured to perform adaptive functions based on the results of a diagnostic test. In the example of FIG. 3D, the detection of low impedance indicates a normal condition such that no corrective action may be required. If high impedance is detected (i.e., there is an increase of the impedance of the power/data transmission line), then the level at which power is transmitted through the electrical lead assembly 306 can be automatically increased in order to compensate for the power losses resulting from the increased impedance.

As noted, the continuity test may determine that an open circuit exists in the electrical lead assembly 306. When an open circuit is detected, the diagnostic and adaptive circuitry 320 can be configured to automatically terminate the current flow through the electrical lead assembly 306 to prevent damage to the device (i.e., module 302).

A third type of diagnostic test may be performed to detect low impedance (indicating a short circuit) between either of the wires 340 and 342 inside of the electrical lead assembly 306 and the external electrode 322. This test, sometimes referred to herein as an "external leakage current test," evaluates the electrical insulation of the wires 340 and 342 to determine if current is leaking from the electrical lead assembly 306 into the recipient's body (i.e., the surrounding tissue and/or body fluid). In an external leakage current test, each of the wires 340 and 342 is tested separately. As such, FIG. 3E illustrates the configuration to perform the external leakage current test for wire 340, while FIG. 3F illustrates the configuration to perform external leakage current test for wire 342.

Figure 3E:
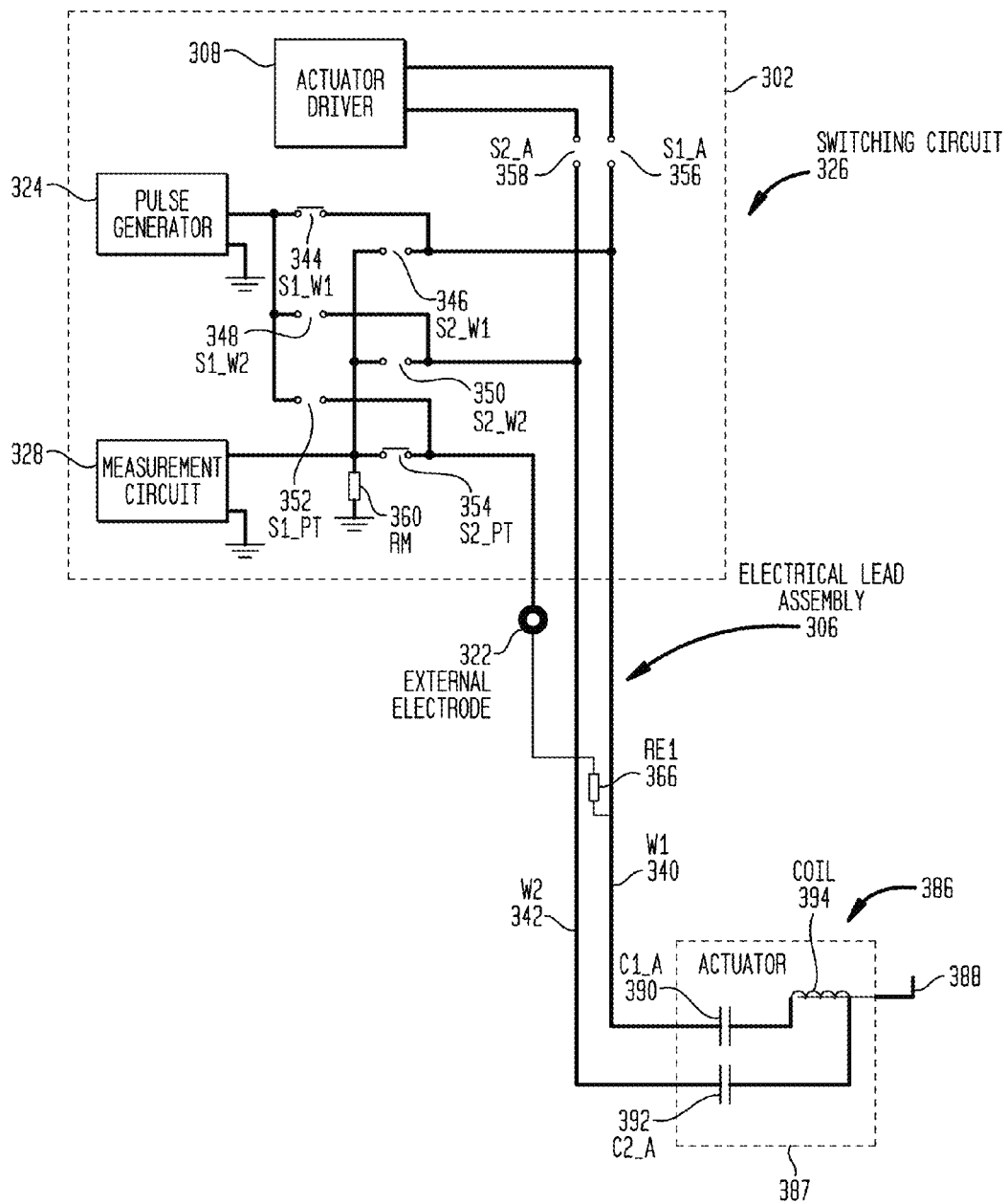
FIG. 3E is a schematic circuit diagram illustrating a configuration for diagnostic and adaptive circuitry in accordance with embodiments presented herein.
Figure 3F:
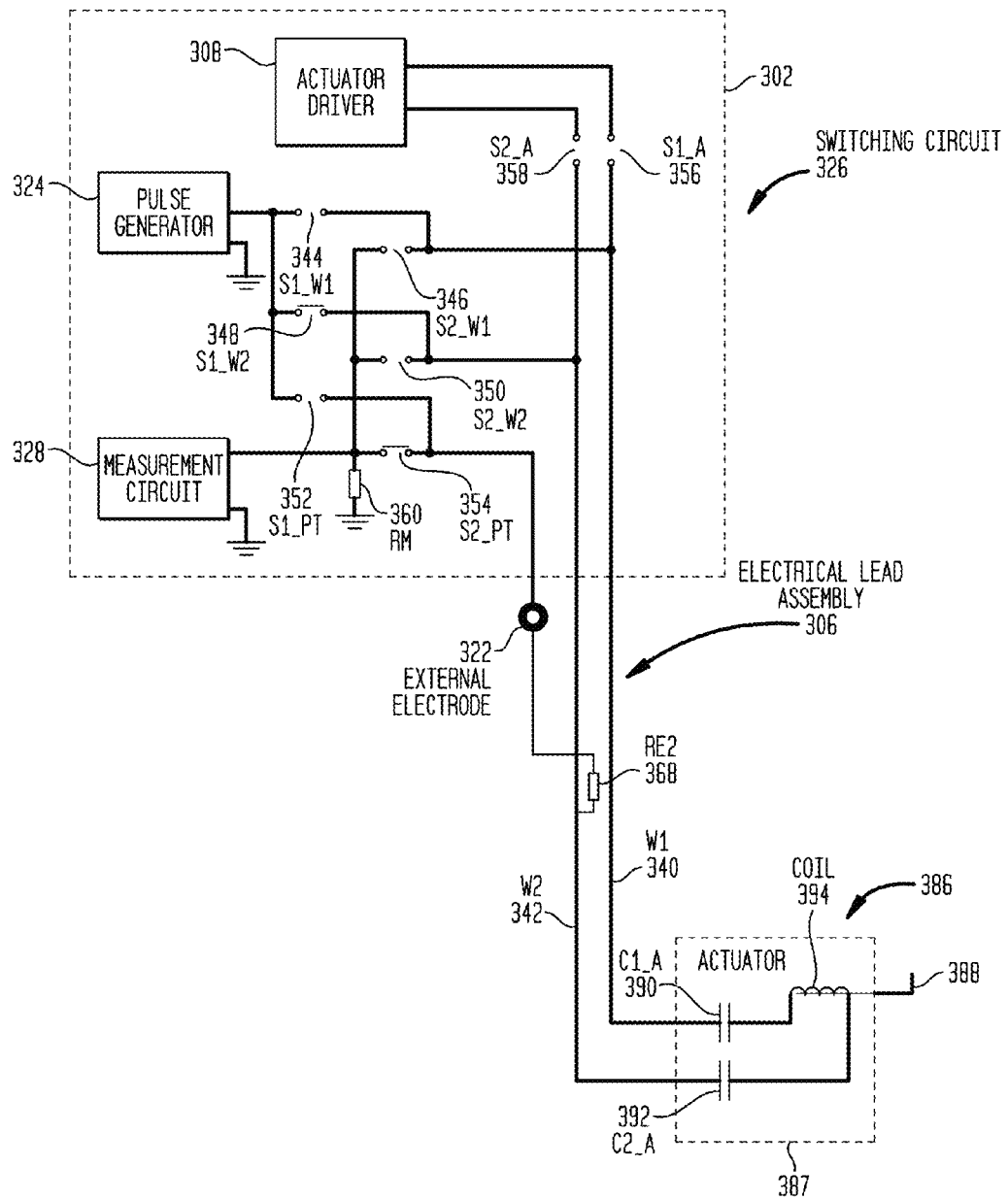
FIG. 3F is a schematic circuit diagram illustrating a configuration for diagnostic and adaptive circuitry in accordance with embodiments presented herein.

FIG. 3E illustrates a resistor 366 (RE1) within electrical lead assembly 306. The resistor 366 shown in FIG. 3E is not an actual resistor, but instead represents the impedance between the wire 340 and the external electrode 322. Similarly, FIG. 3F illustrates a resistor 368 (RE2) within electrical lead assembly 306. Again, the resistor 368 shown in FIG. 3F is not an actual resistor, but instead represents the impedance between the wire 342 and the external electrode 322.

To perform the leakage current test of wire 340 (i.e., measure the leakage current from wire 340 to the recipient's tissue outside of the lead assembly 306), a voltage pulse is applied to the wire 340 and the external electrode 322 through the measurement resistor 360. If there is no leakage current path between wire 340 and the external electrode 322 (i.e., RE1=∞), then there will be no current flow between the wire 340 and the external electrode 322. As such, the voltage over the measurement resistor 360 will be zero. If there is a leakage current path between the wire 340 and the external electrode 322, then there will be a leakage current flow through the recipient's tissue (i.e., through switch 344, wire 340, the recipient's tissue (RE1), external electrode 322, switch 354, and measurement resistor 360 to ground) resulting in a voltage drop over the measurement resistor 360. The voltage across the measurement resistor 360, measured at the end of the voltage pulse by the measurement circuit 328, is proportional to the amplitude of the leakage current between wire 340 and the external electrode 322. Therefore, the measurement circuit 328 can use the voltage level measured at the end of the pulse to quantify the leakage current between the wire 340 and the external electrode 322. That is, the measurement circuit 328 is not only configured to detect the presence of current leakage between the wire 340 and the external electrode 322, but rather may also be configured to determine a magnitude of the current leakage.

In FIG. 3E, the test signal is applied on wire 340 and the external electrode 322. If there is a leakage path from wire 340 to the external electrode 322, than a leakage current ($I_{LW1}$) with a constant amplitude will flow. The current amplitude is defined by the value of the resistance through the recipient's tissue between the wire 340 and external electrode 322. The current path is wire 340, RE1, external electrode 322, measurement resistor 360, and ground. In this case, the voltage over the measurement resistor 360 may be denoted is Vw1.

If there is a leakage path from wire 342 to the external electrode 322, than a leakage current ($I_{LW2}$) with exponentially decreasing amplitude (due to charging of capacitors 390 and 392) will flow. The initial current amplitude is defined by the value of the resistance through the recipient's tissue between wire 342 and the external electrode 322. The current path is wire 340, capacitor 390, coil 394, capacitor 392, wire 342, the recipient's tissue, external electrode 322, measurement resistor 360, and ground.

If there is a leakage path from the coil 394 to the external electrode 322, then a leakage current ($I_{LC}$) with exponentially decreasing amplitude (due to charging of capacitor 390) will flow. The initial current amplitude is defined by the value of the resistance of the recipient's tissue, etc. between the coil 394 and the external electrode 322, and the current path is wire 340, capacitor 390, coil 394, the recipient's tissue, external electrode 322, measurement resistor 360, and ground. The voltage over the measurement resistor 360 is measured at the end of the test (long duration) pulse, when capacitors 390 and 392 (for leakage from wire 342) or capacitor 390 (for leakage from coil 394) are fully charged and $I_{LW2}$ or $I_{LC}$ is equal to zero. Thus the voltage is proportional to $I_{LW1}$. If there is no leakage path from wire 340 (Rw1=∞), then the voltage at the measurement resistor 360 is zero.

To perform the leakage current test of wire 342 (i.e., measure the leakage current from wire 342 to the recipient's tissue outside of the lead assembly 306), a voltage pulse is applied to the wire 342 and the external electrode 322 through the measurement resistor 360. If there is no leakage current path between wire 342 and the external electrode 322 (i.e., RE2=∞), then there will be no current flow between the wire 342 and the external electrode 322. As such, the voltage over the measurement resistor 360 will be zero. If there is a leakage current path between the wire 342 and the external electrode 322, then there will be a leakage current flow through the recipient's tissue (i.e., through switch 348, wire 342, the recipient's tissue (RE2), external electrode 322, switch 354, and measurement resistor 360 to ground) resulting in a voltage drop over the measurement resistor 360. The voltage across the measurement resistor 360, measured at the end of the voltage pulse by the measurement circuit 328, is proportional to the amplitude of the leakage current between wire 342 and the external electrode 322. Therefore, the measurement circuit 328 can use the voltage level measured at the end of the pulse to quantify the leakage current between the wire 342 and the external electrode 322. That is, the measurement circuit 328 is not only configured to detect the presence of current leakage between the wire 342 and the external electrode 322, but rather may also be configured to determine a magnitude of the current leakage.

In FIG. 3F, the test signal is applied on wire 342 and the external electrode 322. If there is a leakage path from wire 342 to the external electrode 322, than a leakage current ($I_{LW2}$) with a constant amplitude will flow. The current amplitude is defined by the value of the resistance through the recipient's tissue between the wire 342 and external electrode 322. The current path is wire 342, RE2, external electrode 322, measurement resistor 360, and ground. In this case, the voltage over the measurement resistor 360 may be denoted is Vw2.

If there is a leakage path from wire 340 to the external electrode 322, than a leakage current ($I_{LW1}$) with exponentially decreasing amplitude (due to charging of capacitors 390 and 392) will flow. The initial current amplitude is defined by the value of the resistance through the recipient's tissue between wire 340 and the external electrode 322. The current path is wire 342, capacitor 390, coil 394, capacitor 392, wire 340, the recipient's tissue, external electrode 322, measurement resistor 360, and ground.

If there is a leakage path from the coil 394 to the external electrode 322, then a leakage current ($I_{LC}$) with exponentially decreasing amplitude (due to charging of capacitor 392) will flow. The initial current amplitude is defined by the value of the resistance of the recipient's tissue, etc. between the coil 394 and the external electrode 322, and the current path is wire 342, capacitor 392, coil 394, the recipient's tissue, external electrode 322, measurement resistor 360, and ground. The voltage over the measurement resistor 360 is measured at the end of the test (long duration) pulse, when capacitors 390 and 392 (for leakage from wire 340) or capacitor 390 (for leakage from wire 342) are fully charged and $I_{LW2}$ or $I_{LC}$ is equal to zero. Thus the voltage is proportional to $I_{LW1}$. If there is no leakage path from wire 342 (Rw1=∞), then the voltage at the measurement resistor 360 is zero.

As noted above, the diagnostic and adaptive circuitry 320 is configured to perform adaptive functions based on the results of a diagnostic test. In the examples of FIGS. 3E and 3F, the detection of a leakage current between one of the wires 340 and 342 and the external electrode 322 indicates that there is a deterioration of the electrical insulation of the corresponding wire. As a result, the diagnostic and adaptive circuitry 320 can be configured to automatically limit or terminate the current flow through the electrical lead assembly 306 to prevent tissue damage resulting from a current leak. The diagnostic and adaptive circuitry 320 may also be configured to transmit the results of the external leakage current test to the external device (e.g., external processor, remote control, clinician equipment, etc.) via the telemetry circuit 332 and the implantable coil 339. The telemetry circuit 332 may be configured to transmit, for example, an indication that a current leakage has been detected, an indication of the which wire has experienced a current leak, an indication of the magnitude of the current leakage, and/or an indication of the corrective action taken by the diagnostic and adaptive circuitry 320. The transmission by the telemetry circuit 332 may occur in real-time (i.e., if an external device is present) or the transition may occur at a later time. As such, the diagnostic and adaptive circuitry 320 may have the ability to temporarily store testing results for subsequent transmission/upload to an external device.

Figure 3G:
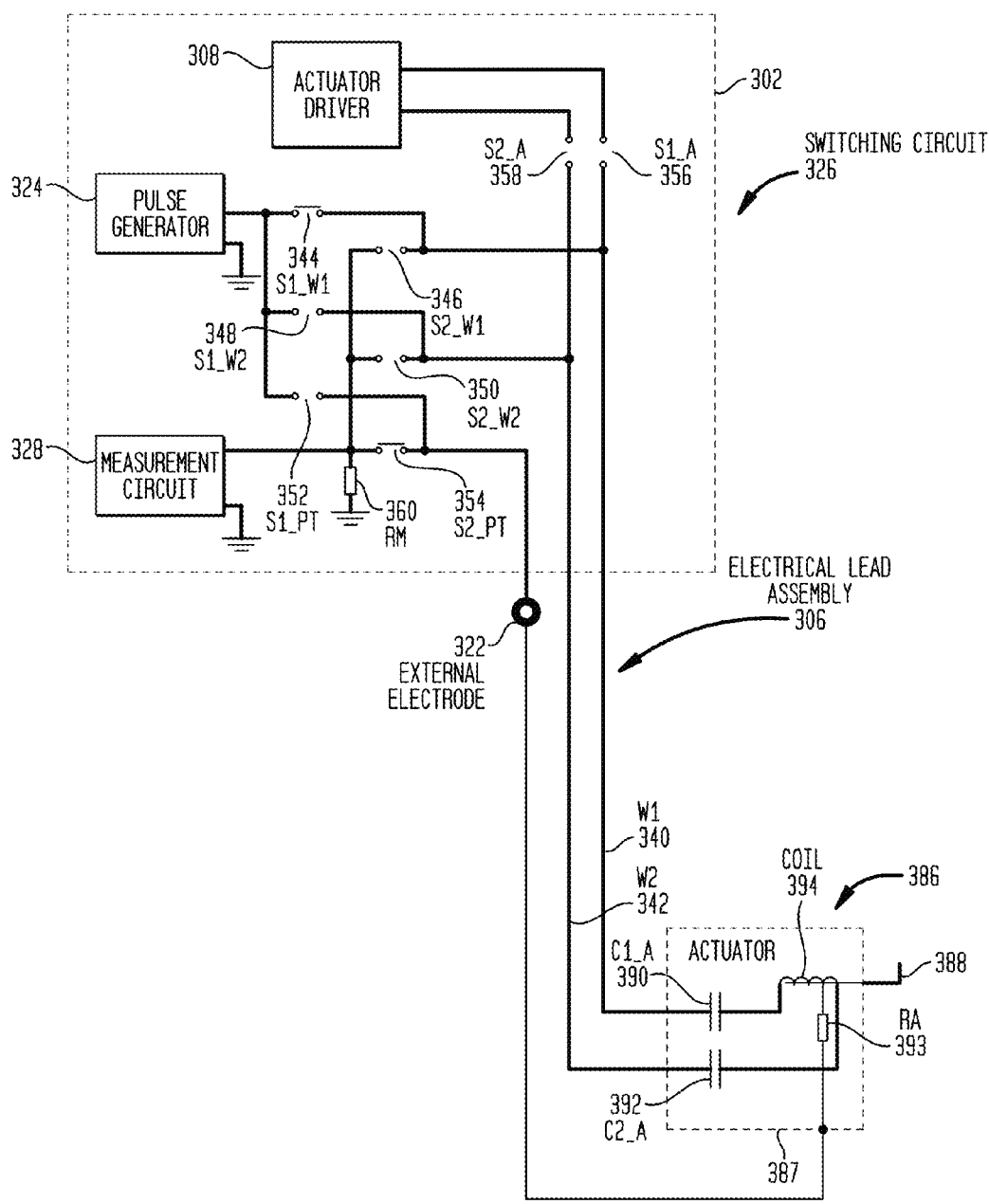
FIG. 3G is a schematic circuit diagram illustrating a configuration for diagnostic and adaptive circuitry in accordance with embodiments presented herein.
Figure 3H:
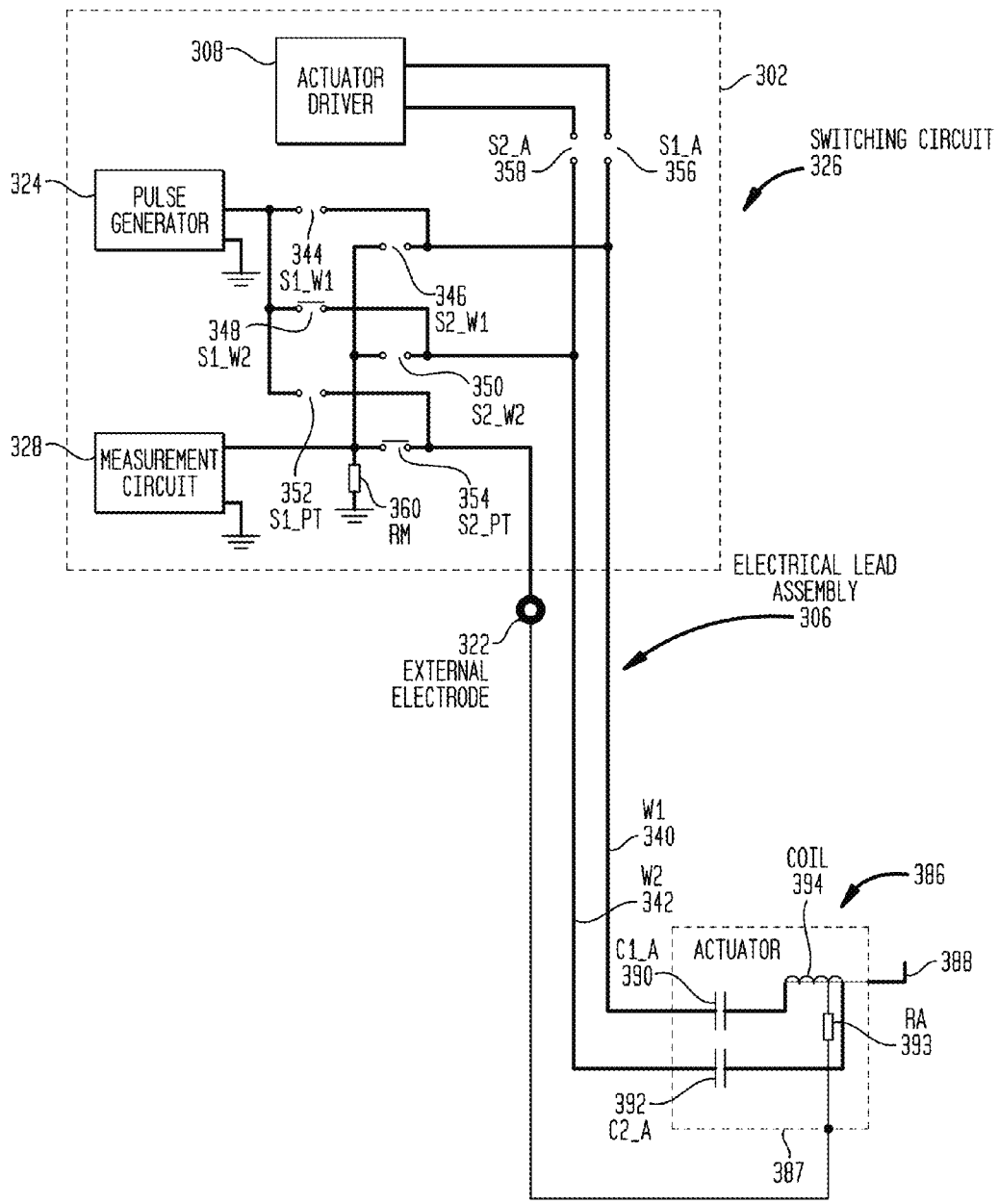
FIG. 3H is a schematic circuit diagram illustrating a configuration for diagnostic and adaptive circuitry in accordance with embodiments presented herein.

A fourth type of diagnostic test may be performed to detect/measure in vivo insulation fault of the actuator coil 394. This test, sometimes referred to herein as an "actuator coil insulation test," evaluates the insulation between the coil 394 and the actuator housing 387. FIGS. 3G and 3H illustrate two configurations to perform actuator coil insulation tests.

FIGS. 3G and 3H each illustrate a resistor 393 (RA) within the actuator 386. The resistor 393 is not an actual resistor, but instead represents the insulation impedance (resistance) between the coil 394 and the housing 387. The actuator coil insulation test evaluates the insulation between the coil 394 and the actuator housing 387 by determining if there is any current leakage into the recipient's tissue.

More specifically, in FIG. 3G a voltage pulse is applied to the wire 340 and the external electrode 322 through the measurement resistor 360. If there is no leakage current path between the coil 394 and the housing 387 (i.e., RA=∞), then there will be no current flow from the coil 394 to housing 387 and from housing 387 through the recipient's tissue to the external electrode 322. As such, the voltage over the measurement resistor 360 will be zero. If there is a leakage current path between the coil 394 and the housing 387, then there will be a leakage current flow through the recipient's tissue to the external electrode 322 resulting in a voltage drop over the measurement resistor 360.

The initial amplitude of the current is proportional to the impedance of the current path (i.e., the current path defined by switch 344, wire 340, capacitor 390, coil 394, RA 393 to housing 387, the recipient's tissue, external electrode 322, switch 354, and the measurement resistor 360). Thereafter, the current exponentially decreases as the capacitor 390 charges. The initial voltage measured across the measurement resistor 360 by the measurement circuit 328 is proportional to the insulation impedance between the coil 394 and the housing 387.

In FIG. 3H, a voltage pulse is applied to the wire 342 and the external electrode 322 through the measurement resistor 360. If there is no leakage current path between the coil 394 and the housing 387 (i.e., RA=∞), then there will be no current flow from the coil 394 to the housing 387 and from housing 387 through the recipient's tissue to the external electrode 322. As such, the voltage over the measurement resistor 360 will be zero. If there is a leakage current path between the coil 394 and the housing 387, then there will be a leakage current flow from the coil 394 to the housing 387 and from housing 387 through the recipient's tissue to the external electrode 322 resulting in a voltage drop over the measurement resistor 360.

The initial amplitude of the current is proportional to the impedance of the current path (i.e., the current path defined by switch 348, wire 342, capacitor 392, coil 394, RA 393 to housing 387, the recipient's tissue, external electrode 322, switch 354, and the measurement resistor 360). Thereafter, the current exponentially decreases as the capacitor 392 charges. The initial voltage measured across the measurement resistor 360 by the measurement circuit 328 is proportional to the insulation impedance between the coil 394 and the housing 387.

For FIG. 3G, the test signal is applied on wire 340 and the external electrode 322 and the amplitude of the initial peak is measured. If there is a leakage path from the coil 394 to the external electrode 322, then a leakage current ($I_{LC}$) with exponentially decreasing amplitude (due to charging of 390) will flow. The initial current amplitude is defined by the value of the resistance (initially there is no charge over the capacitor 390) and the current path is wire 340, capacitor 390, coil 394, the resistance of the recipient's tissue, etc., external electrode 322, measurement resistor 360, and ground. The initial voltage peak over the measurement resistor 360 is proportional to $I_{LC}$.

If there are multiple leakage paths at coil 394 and wires 340 or 342, then the initial peak will be proportional to the sum of all leakage currents ($I_{Lsum}$). The value of $I_{LC}$ can be calculated using the results obtained in FIG. 3E ($I_{LW1}$) and FIG. 3F ($I_{LW2}$) (e.g., $I_{LC}=I_{Lsum}-(I_{LW1}+I_{LW2})$).

For FIG. 3H, the test signal is applied on wire 342 and the external electrode 322 and the amplitude of the initial peak is measured. If there is a leakage path from the coil 394 to the external electrode 322, then a leakage current ($I_{LC}$) with exponentially decreasing amplitude (due to charging of capacitor 392) will flow. The initial current amplitude is defined by the value of the resistance (initially there is no charge over the capacitor 392) and the current path is wire 342, capacitor 392, coil 394, the resistance of the recipient's tissue, etc., external electrode 322, measurement resistor 360, and ground. If there are multiple leakage paths at coil 394 and wires 340 or 342, then the initial peak will be proportional to the sum of all leakage currents ($I_{Lsum}$). The value of $I_{LC}$ can be calculated using the results obtained in FIG. 3E ($I_{LW1}$) and FIG. 3F ($I_{LW2}$) (e.g., $I_{LC}=I_{Lsum}-(I_{LW1}+I_{LW2})$).

As noted above, the diagnostic and adaptive circuitry 320 is configured to perform adaptive functions based on the results of a diagnostic test. In the examples of FIGS. 3G and 3H, the detection of a leakage current between the coil 394 and the external electrode 322 indicates that there is a deterioration of the electrical insulation of the coil 394. As a result, the diagnostic and adaptive circuitry 320 can be configured to automatically limit the current flow through the electrical lead assembly 306 to prevent further damage to the device (actuator 386). The diagnostic and adaptive circuitry 320 may also be configured to transmit the results of the external leakage current test to the external device (e.g., external processor, remote control, clinician equipment, etc.) via the telemetry circuit 332 and the implantable coil 339. The telemetry circuit 332 may be configured to transmit, for example, an indication that a current leakage has been detected, an indication of the magnitude of the current leakage, and/or an indication of the corrective action taken by the diagnostic and adaptive circuitry 320. The transmission by the telemetry circuit 332 may occur in real-time (i.e., if an external device is present) or the transition may occur at a later time. As such, the diagnostic and adaptive circuitry 320 may have the ability to temporarily store testing results for subsequent transmission/upload to an external device.

In operation, switches 346, 350, and 352 may be used to reverse the direction of the leakage current through the leakage path. When current leakage is detected between one of the wire 340, wire 342, or coil 394 and the external electrode 322, the reverse direction of the leakage current through the leakage path is needed in order to balance the charge delivered and eliminate electrode polarization effect in the recipient's tissue that results when the leakage current flows through the body. The reverse of the test current flow is used for all tests (internal leakage, continuity and external leakage), but it is particularly important for the external leakage test.

Figure 4:
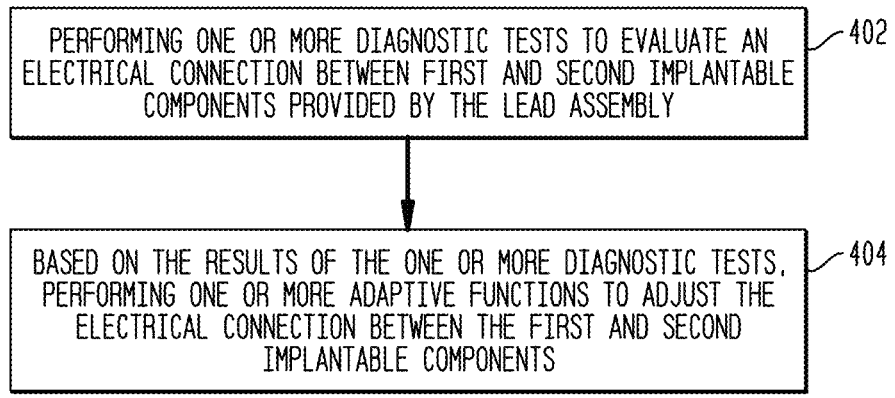
FIG. 4 is a flowchart of a method in accordance with embodiments presented herein.

FIG. 4 is a high-level flowchart illustrating a method 400 performed in an implantable hearing prosthesis comprising first and second physically separate implantable components connected by an lead assembly. Method 400 begins at 402 wherein one or more diagnostic tests are performed to evaluate the electrical connection between first and second implantable components provided by the lead assembly. At 404, based on the results of the one or more diagnostic tests, one or more adaptive functions are performed to adjust the electrical connection between the first and second implantable components.

In one embodiment, an electrical insulation test is performed to detect low impedance between a pair of conductors forming part of the electrical connection. In such an embodiment, upon detecting low impedance between the pair of conductors, current flow through the pair of conductors may be automatically stopped or reduced (limited).

In another embodiment, a conductor continuity test may be performed to detect high impedance at a wire forming part of the electrical connection. In such an embodiment, upon detecting high impedance at the wire forming part of the electrical connection, current flow through the wire may be increased to compensate for the high impedance on the wire.

In a further embodiment, an electrical insulation test may be performed to detect low impedance between a wire forming part of the electrical connection and an external reference point (i.e., to detect current leakage from the wire into a recipient's tissue). In such an embodiment, upon detecting low impedance between the wire forming part of the electrical connection and the external reference point, current flow through the wire may be automatically terminated (stopped).

In certain embodiments, the method 400 may further include transmitting, to an external device, at least one of results of the diagnostic tests or indications of performed adaptive functions.

The diagnostic and adaptive circuitry in accordance with embodiments of the present invention has been described with reference to three illustrative implantable hearing prosthesis, namely two different cochlear implants and one direct acoustic cochlear stimulator. It is to be appreciated that the diagnostic and adaptive circuitry may be used in any implantable hearing prosthesis that has two or more physically separate implantable components connected by an electrical connection (e.g., lead assembly, cable, connector, etc.) comprising one or more wire pairs (e.g., any a two-wire link, four-wire link, etc.)

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable hearing prosthesis, comprising:
    a first implantable component;
    a second implantable component electrically connected to the first implantable component;
    a physical electrical connection between the first and second implantable components, wherein the electrical connection is configured for electrical signal transfer between the first and second implantable components; and
    diagnostic and adaptive circuitry having a plurality of arrangements, wherein each arrangement of the diagnostic and adaptive circuitry enables the performance of one of a plurality of diagnostic tests that each evaluate a different attribute of the electrical connection between the first and second implantable components, and wherein the diagnostic and adaptive circuitry is configured to, based on the results of one or more of the diagnostic tests, perform one or more adaptive functions to change operation of the electrical signal transfer between the first and second implantable component via the electrical connection.

2. The implantable hearing prosthesis of claim 1, wherein the electrical connection comprises a pair of conductors, and wherein in one of the plurality of arrangements, the diagnostic and adaptive circuitry is configured to perform a diagnostic test to detect low impedance between the pair of conductors.

3. The implantable hearing prosthesis of claim 2, wherein upon detecting low impedance between the pair of conductors, the diagnostic and adaptive circuitry is configured to change operation of the electrical signal transfer between the first and second implantable component via the electrical connection by at least one of automatically stopping or limiting current flow through the pair of conductors.

4. The implantable hearing prosthesis of claim 1, wherein the electrical connection comprises a wire, and wherein in one of the plurality of arrangements, the diagnostic and adaptive circuitry is configured to perform a diagnostic test to detect high impedance at the wire.

5. The implantable hearing prosthesis of claim 4, wherein upon detecting high impedance at the wire, the diagnostic and adaptive circuitry is configured to change operation of the electrical signal transfer between the first and second implantable component via the electrical connection by automatically increase current flow through the wire.

6. The implantable hearing prosthesis of claim 1, wherein the electrical connection comprises a wire and the diagnostic and adaptive circuitry includes an electrode located external to the electrical connection, and wherein in one of the plurality of arrangements, the diagnostic and adaptive circuitry is configured to perform a diagnostic test to detect low impedance between the wire and the electrode.

7. The implantable hearing prosthesis of claim 6, wherein upon detecting low impedance between the wire and the electrode, the diagnostic and adaptive circuitry is configured to operation of the electrical signal transfer between the first and second implantable component via the electrical connection by automatically stop current flow through the wire.

8. The implantable hearing prosthesis of claim 1, wherein the diagnostic and adaptive circuitry includes a switching circuit and a controller, wherein the controller is configured to actuate the switching circuit to switch the diagnostic and adaptive circuitry between a first one of the plurality of arrangements and a second one of the plurality of arrangements.

9. The implantable hearing prosthesis of claim 8, wherein the first implantable component comprises a stimulator module, and wherein the controller is configured to switch the switching circuit between a stimulation operational mode in which power is supplied to a stimulator module in the first implantable component and a diagnostic operational mode that enables performance of the plurality of diagnostic tests.

10. The implantable hearing prosthesis of claim 1, wherein the first implantable component is a cochlear implant main module comprising a stimulator module comprising a stimulator and the second implantable component is a secondary module that comprises a battery.

11. The implantable hearing prosthesis of claim 10, wherein the secondary module further comprises a sound processor and a microphone.

12. The implantable hearing prosthesis of claim 1, wherein the first implantable component is a stimulator module comprising a stimulator and the second implantable component is an implantable microphone.

13. The implantable hearing prosthesis of claim 1, wherein the first implantable component is a stimulator module comprising an actuator driver and the second implantable component is a physically separate mechanical actuator.

14. The implantable hearing prosthesis of claim 1, further comprising an external device, wherein the diagnostic and adaptive circuitry includes a telemetry circuit configured to transmit at least one of results of the diagnostic tests or indications of performed adaptive functions to the external device.

15. A method performed in an implantable hearing prosthesis comprising a switching circuit and first and second physically separate implantable components connected by a lead assembly, the method comprising:
actuating the switching circuit to a stimulation operational mode arrangement in which the switching circuit enables power to be supplied from the first implantable component to the second implantable components;
switching the switching circuit from the stimulation operational mode arrangement to a diagnostic operational mode arrangement in which the switching circuit enables the performance of one or more diagnostic tests to evaluate an electrical connection between the first and second implantable components;
while the switching circuit is in the at least one diagnostic operational mode arrangement, performing the one or more diagnostic tests to evaluate an electrical connection between the first and second implantable components provided by the lead assembly; and
based on the results of the one or more diagnostic tests, performing one or more adaptive functions to adjust operation of the electrical connection between the first and second implantable components.

16. The method of claim 15, wherein performing one or more diagnostic test to evaluate the electrical connection comprises performing an electrical insulation test to detect low impedance between a pair of conductors forming part of the electrical connection; and
wherein, upon detecting low impedance between the pair of conductors, performing one or more adaptive functions to adjust operation of the electrical connection comprises at least one of automatically stopping or limiting current flow through the pair of conductors.

17. The method of claim 15, wherein performing one or more diagnostic test to evaluate the electrical connection comprises performing a conductor continuity test to detect high impedance at a wire forming part of the electrical connection; and
wherein, upon detecting high impedance at the wire forming part of the electrical connection, performing one or more adaptive functions to adjust operation of the electrical connection comprises automatically increasing current flow through the wire.

18. The method of claim 15, wherein performing one or more diagnostic tests to evaluate the electrical connection comprises performing an electrical insulation test to detect low impedance between a wire forming part of the electrical connection and an external reference point; and
wherein, upon detecting low impedance between the wire forming part of the electrical connection and the external reference point, performing one or more adaptive functions to adjust operation of the electrical connection comprises automatically stopping current flow through the wire.

19. The method of claim 15, further comprising:
transmitting, to an external device, at least one of results of the diagnostic tests or indications of performed adaptive functions.

20. An implantable hearing prosthesis, comprising:
first and second physically separate implantable components;
a cable electrically connecting the first and second implantable components to enable current flow between the first and second implantable components; and
circuitry in the first implantable component, wherein the circuitry includes a switching circuit having a plurality of different arrangements each enabling performance of a specific one of a plurality of diagnostic tests each configured to evaluate different electrical attributes of the cable and to adapt current flow through the cable based on the evaluation of the electrical attributes.

21. The implantable hearing prosthesis of claim 20, wherein the cable includes a pair of conductors, and wherein the circuitry is configured to detect low impedance between the pair of conductors in the cable and to automatically stop or limit current flow through the pair of conductors.

22. The implantable hearing prosthesis of claim 20, wherein the cable includes a wire, and wherein the circuitry is configured to detect high impedance at the wire in the cable and to automatically increase current flow through the wire.

23. The implantable hearing prosthesis of claim 20, further comprising an electrode located external to the cable, wherein the cable includes a wire, and wherein the circuitry is configured to detect low impedance between the wire in the cable and the electrode located external to the cable and to automatically stop current flow through the wire.

\* \* \* \* \*